US007220726B2

(12) United States Patent
Andersson et al.

(10) Patent No.: US 7,220,726 B2
(45) Date of Patent: *May 22, 2007

(54) ANTIFUNGAL PIMARICIN COMPOSITIONS AND THERAPEUTIC METHODS EMPLOYING SAME

(75) Inventors: Borje S. Andersson, Houston, TX (US); Elias J. Anaissie, Little Rock, AR (US)

(73) Assignee: Board of Regents, The University of Texas System, Austin, TX (US)

( * ) Notice: Subject to any disclaimer, the term of this patent is extended or adjusted under 35 U.S.C. 154(b) by 372 days.

This patent is subject to a terminal disclaimer.

(21) Appl. No.: 10/439,252

(22) Filed: May 15, 2003

(65) Prior Publication Data

US 2004/0037907 A1 Feb. 26, 2004

Related U.S. Application Data

(62) Division of application No. 09/415,890, filed on Oct. 8, 1999, now Pat. No. 7,153,838.

(51) Int. Cl.
*A61K 31/7008* (2006.01)
*A61K 9/107* (2006.01)
*A61K 25/02* (2006.01)

(52) U.S. Cl. .................... 514/31; 424/405; 424/406; 424/450; 514/937; 514/938; 514/970; 514/974

(58) Field of Classification Search ............... 424/405, 424/406, 450; 514/937, 943, 31, 32, 643, 514/938, 970, 974
See application file for complete search history.

(56) References Cited

U.S. PATENT DOCUMENTS

| | | | |
|---|---|---|---|
| 3,343,958 A | 9/1967 | Morse | 430/251 |
| 3,892,850 A | 7/1975 | Struyk et al. | 424/119 |
| 4,148,891 A | 4/1979 | Smink | 424/181 |
| 4,409,205 A * | 10/1983 | Shively | 424/78.04 |
| 4,536,494 A | 8/1985 | Carter | 514/31 |
| 4,600,706 A | 7/1986 | Carter | 514/31 |
| 4,766,046 A | 8/1988 | Abra et al. | 424/450 |
| 4,794,117 A | 12/1988 | Corbiere | 514/420 |
| 4,883,785 A | 11/1989 | Chow et al. | 514/31 |
| 4,950,477 A | 8/1990 | Schmitt et al. | 424/43 |
| 5,006,595 A | 4/1991 | Smith et al. | 524/548 |
| 5,277,914 A | 1/1994 | Szoka, Jr. | 424/450 |
| 5,430,057 A | 7/1995 | Andersson et al. | 514/517 |
| 5,552,151 A | 9/1996 | Noordam et al. | 424/439 |
| 5,559,148 A | 9/1996 | Andersson et al. | 514/517 |
| 5,597,598 A * | 1/1997 | van Rijn et al. | 426/310 |
| 5,651,991 A | 7/1997 | Sugiyama et al. | 424/502 |
| 5,693,337 A * | 12/1997 | Suzuki et al. | 424/450 |
| 5,821,233 A | 10/1998 | Van Rijn et al. | 514/31 |
| 5,877,205 A | 3/1999 | Andersson | 514/449 |
| 6,045,815 A * | 4/2000 | Andersson et al. | 424/405 |
| 6,107,333 A | 8/2000 | Andersson | 514/449 |
| 6,291,500 B2 | 9/2001 | Ponikau | 514/393 |
| 6,369,036 B1 | 4/2002 | Van Rijn et al. | 514/31 |
| 6,406,713 B1 | 6/2002 | Janoff et al. | 424/450 |
| 6,844,004 B2 * | 1/2005 | Andersson | 424/405 |
| 2002/0155141 A1 * | 10/2002 | Andersson | 424/406 |

FOREIGN PATENT DOCUMENTS

| | | | |
|---|---|---|---|
| DE | 3036320 | * | 6/1982 |
| DE | 3819504 | | 12/1989 |
| EP | 0664130 | | 7/1995 |
| GB | 2 106 498 A | | 4/1983 |
| GB | 2 116 425 A | | 9/1983 |
| WO | WO 93/07884 | | 4/1993 |
| WO | WO 96/29998 | | 10/1996 |

OTHER PUBLICATIONS

Kejda et al (Mykosen, 1970, 13 No. 1, 19-24. (ABS).*
Kedja, J., "Local treatment of chronic paronychia with pimaricin-dimethyl-sulfoxide (DMSO) suspension," Abstract No. 35097, *Chemical Abstracts*, 79: No. 6, Columbus, Ohio, 1973.
Drug Facts and Comparisons, Wolters Kluwer Co., St. Louis, MO, , Intravenous Nutritional Therapy, p. 138 (1977 edition).
Drug Information for the Health Care Professional: USPDI, p. 1705, (1989 edition).
Korteweg et al., "Some pharmacological properties of Pimaricin and possible clinical application of this antifungal antibiotic," *Iind int. Symp. Chemotherapy*, 261-272, 1963.
Raab, ":Natamycin (Pimaricin) its properties and Possibilities in medicine," 1-134, Georg Thieme Publishers Stuttgart, 1972.
Spiegel et al., "Use of Nonaqueous Solvents in Parenteral Products," Journal of Pharmaceutical Sciences, vol. 52, No. 10, , pp. 917-927 (Oct. 1963).
Yalkowsky et al., "Solubilization of Drugs by Cosolvents," Techniques of Solubilization of Drugs, pp. 91-134, Marcel Dekker Inc., NY (1981).

* cited by examiner

*Primary Examiner*—Alton Pryor
(74) *Attorney, Agent, or Firm*—Fulbright & Jaworski L.L.P.

(57) ABSTRACT

An antifungal composition suitable for parenteral administration to a mammal includes an amount of pimaricin or an antifungal derivative thereof that is effective to inhibit the growth of a fungal infection in a mammal; a pharmaceutically acceptable dipolar aprotic solvent; and a pharmaceutically acceptable aqueous secondary solvent. The composition can be used in methods of preventing or treating a systemic fungal infection in a mammal. The composition can be prepared by dissolving pimaricin or an antifungal derivative thereof in the pharmaceutically acceptable dipolar aprotic solvent; adding to the solution a pharmaceutically acceptable aqueous secondary solvent; and in a preferred method, by subsequently lypohilizing the composition, whereby a dry, shelf-stable composition is produced. This dry composition can be reconstituted into an aqueous solution suitable for parenteral administration.

22 Claims, 15 Drawing Sheets

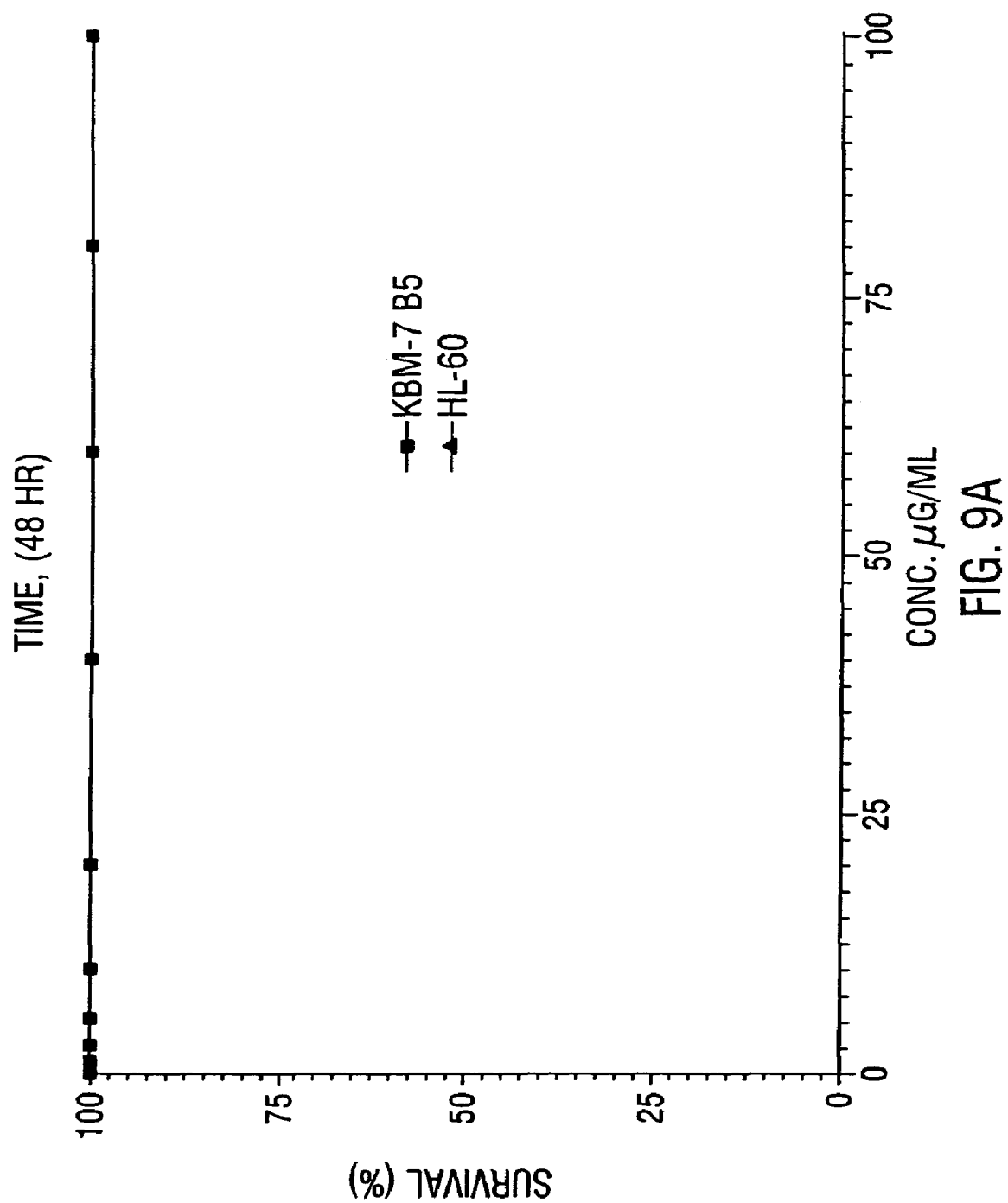

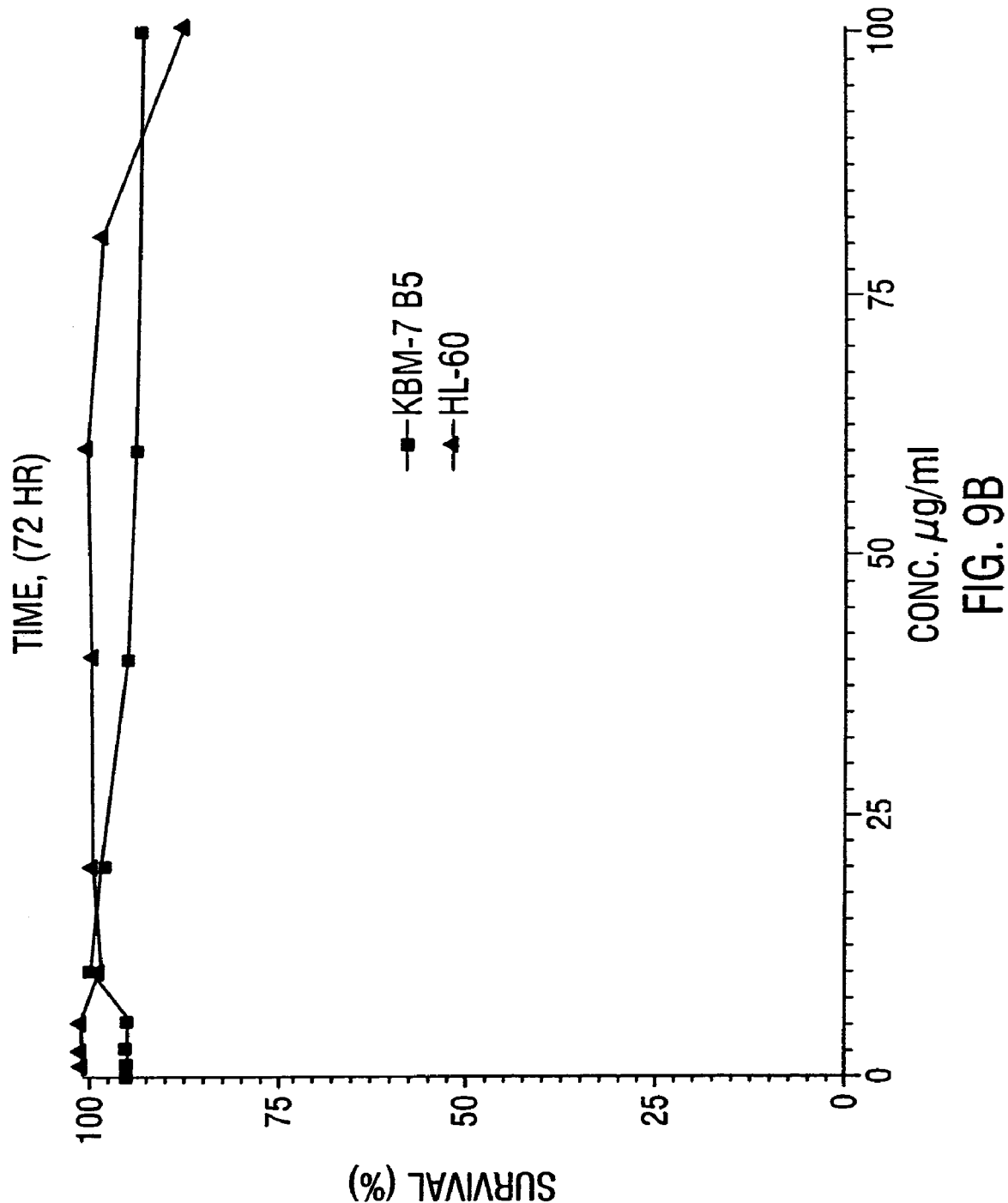

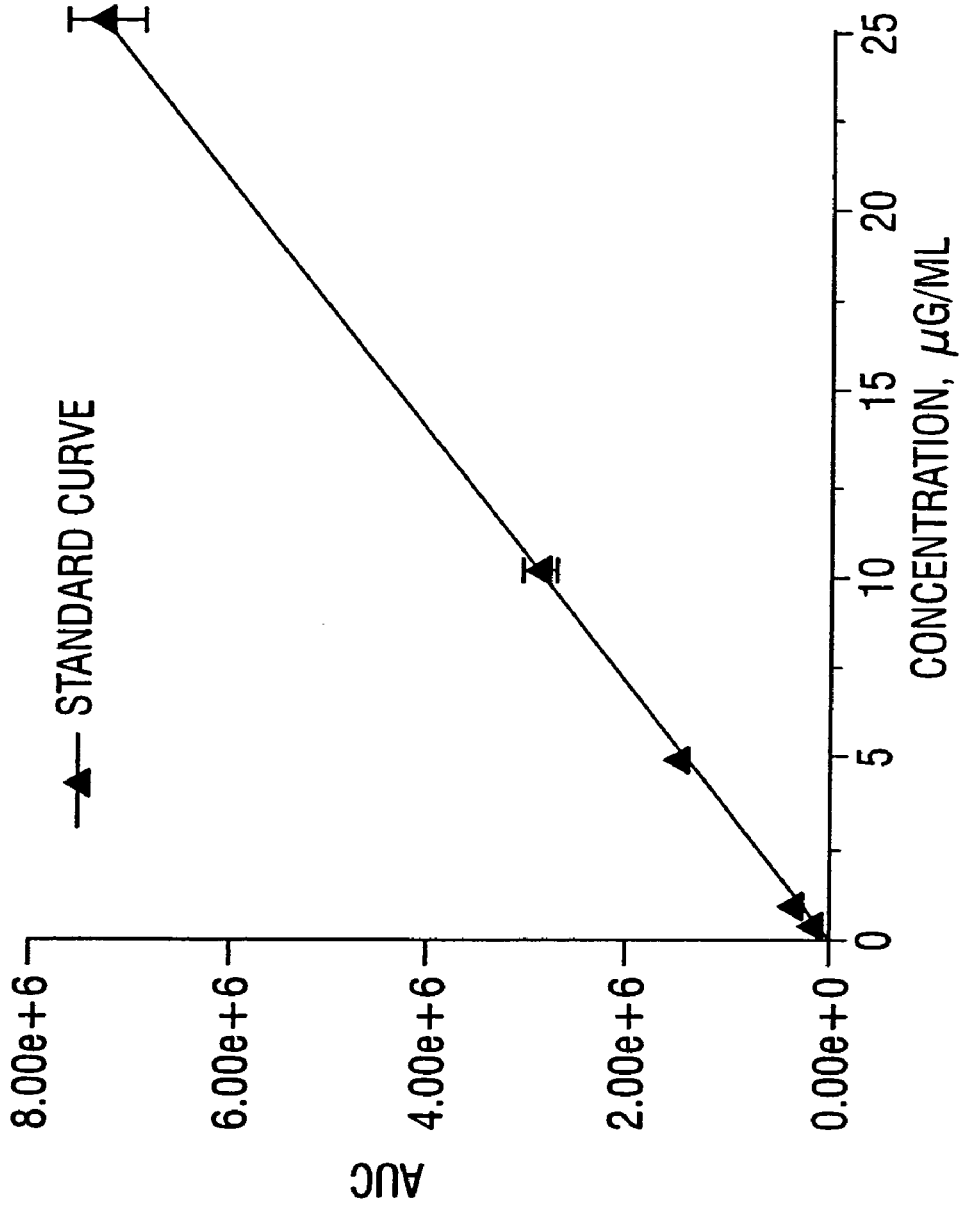

ANTIFUNGAL PIMARICIN COMPOSITIONS AND THERAPEUTIC METHODS EMPLOYING SAME

The present application is a divisional application of application Ser. No. 09/415,890, filed Oct. 8, 1999, now U.S. Pat. No. 7,153,838 which claims the priority of U.S. Ser. No. 08/911,607, filed Aug. 15, 1997, which is now issued as U.S. Pat. No. 6,045,815. The entire text of each of the aboveferenced disclosures is specifically incorporated herein by reference without disclaimer

BACKGROUND OF THE INVENTION

The present invention relates to a drug formulation that is useful for the treatment and suppression of systemic infections, for example those caused by *Aspergillus* and *Fusarium* species.

Disseminated fungal infections constitute one of the most difficult challenges for clinicians caring for patients with hematological cancer (1). While the incidence of hematogenous candidiasis has been significantly reduced with the introduction of fluconazole prophylaxis, the opportunistic molds have became the leading cause of infectious mortality in this patient population (2). Aspergillosis clearly remains the most common mold infection in patients with hematological cancer. However, new opportunistic pathogens have now emerged as a cause of life-threatening infection worldwide. The most frequently reported of these pathogens is *Fusarium* (3–7). Infection with *Fusarium* is associated with a very high mortality and is typically refractory to amphotericin B. Since infection with this organism may mimic aspergillosis, patients are usually treated with Amphotericin B (AMB), an agent with poor activity against Fusariosis. In addition, the airways are the most common primary site of inoculation and infection and are almost always involved in disseminated disease (3–7). Hence, any drug with good activity against Fusariosis (particularly if it is also active against Aspergillosis) that could be given parenterally and also through aerosolization or nebulization will significantly improve our therapeutic armamentarium.

In addition to being ineffective against Fusariosis, Amphotericin B, the first-line treatment for documented or suspected systemic mold infections carries with it common (>75% of treated subjects), substantial and frequently dose-limiting nephrotoxicity, requiring at times hemodialysis. The acute infusion-related adverse events (severe shaking chills, fever, nausea, vomiting, headache) are quite troublesome to patients. Other serious side effects, such as cardiac arrhythmias, bone marrow suppression, neuropathies, and convulsions are also encountered with the use of AMB, although less frequently (8). The introduction of liposomally encapsulated AMB was anticipated to improve the control of systemic fungal infections (9,10). Its administration changed the drug's biodistribution, allowing significantly higher doses to be delivered with (hopefully) better anti-fungal effects, without encountering serious nephrotoxicity (11–13). In spite of an increased renal tolerance to liposomal AMB compared with the parent drug, this new formulation has several limitations, including its high cost (presently around $800 per day) which has limited its use, its toxicity profile which is identical to that of Amphotericin B (except for the kidney toxicity) and the fact that there is no evidence that this new drug formulation has actually improved the ultimate control rate of serious mycotic/mold infections. Liposomal AMB has recently received federal approval for routine clinical use in the U.S.

The only important clinically available alternative to AMB for the treatment of systemic mold infections is itraconazole (Sporinox™) (13, 14, 15). This agent is presently available exclusively as an oral preparation that is only erratically absorbed from the intestinal tract, yielding variable plasma concentrations with highly unpredictable antifungal activity (13) and has little or no activity against *Fusarium*. This bioavailability problem is particularly difficult to manage in bone marrow transplant (BMT) patients who are at highest risk for invasive mold infections. Such patients typically have severe mucositis that interferes with their ability to swallow the itraconazole capsule and also impairs the already erratic intestinal absorption of the drug. In addition, these patients commonly receive antacids or H2 blockers, both agents known to interfere with the absorption of itraconazole.

Based on the above considerations, the development of an effective antimycotic agent with low normal organ toxicity, high bioavailability, predictable pharmacokinetics after parenteral administration, and activity against both *Fusarium* and *Aspergillus* appears highly desirable, Pimaricin, or natamycin (FIG. 1) would fulfill the criterion of being an effective anti-fungal agent, exerting significant activity against molds, particularly *Fusarium* and *Aspergillus*. It was first isolated in 1955 from a strain of *Streptomyces* (15). Pimaricin exhibited a wide range of in vitro activity against fungi, yeast, and trichomonads (15, 16, 17). The drug was found to have little or no toxicity after oral administration, being virtually non-absorbable from the gastrointestinal tract (16, 17). However, the lack of solubility of pimaricin in various solvents, both aqueous and organic, compatible with human administration has severely restricted its use in clinical medicine. Pimaricin's medical utilization is currently confined to the topical treatment of corneal fungal infections (18) and the prevention of such infections in contact-lens users. In contrast, pimaricin's prominent chemical stability paired with its apparent lack of intestinal absorption and systemic toxicity formed the basis for its FDA-approved use in the food industry, where it is used to prevent the proliferation of (aflatoxin-producing) molds (19).

A parenterally acceptable, nontoxic formulation of pimaricin would be potentially beneficial not only for cancer patients, but also for other groups of immunocompromised patients, e.g. those suffering from HIV and those having recently undergone open heart surgery, all of which are commonly targets for opportunistic infections.

Past attempts to solubilize pimaricin in vehicles that are safe for intravascular administration in humans have all failed, despite the hard work by Stuyk and others (15, 16, 17). Thus, Korteweg and coworkers attempted to solubilize the drug by mixing it with a complex polysaccharide (16). Although the water-solubility of this formulation increased dramatically, its antifungal in vitro activity decreased to about ⅓ of that of native *natamycin*. Further, this preparation is comparatively toxic in experimental *animals*, and it was therefore deemed unsuitable for systemic parenteral administration in humans (15).

SUMMARY OF THE INVENTION

One aspect of the present invention is an antifungal composition that is suitable for parenteral administration to a mammal. The composition includes an amount of pimaricin or an antifungal derivative thereof that is effective to inhibit the growth of a systemic infection in a mammal; a pharmaceutically acceptable dipolar aprotic solvent: and a pharmaceutically acceptable aqueous secondary solvent. Suitable dipolar aprotic solvents include N,N-dimethylacetamide (DMA) and dimethyl sulfoxide (DMSO). The aqueous secondary solvent can be, for example water, saline solution, or dextrose solution. It can also be an aqueous lipid emulsion. Suitable aqueous lipid emulsions include those that comprise a lipid component that includes at least one vegetable oil and at least one fatty acid. In one particular embodiment of the invention, the lipid component comprises at least about 5% by weight soybean oil and at least about 50% by weight fatty acids. The lipids in the composition are preferably present in a form other than liposomes (e.g., at least about 50% by weight of the lipid is not in the form of liposomes, more preferably at least about 75%, and most preferably at least about 95%).

Another aspect of the present invention concerns a method of preventing or treating a systemic infection in a mammal. The method comprises administering parenterally to a mammal a composition as described above, in an amount that is effective to inhibit the growth of a systemic infection in the mammal. Although the present invention is especially useful for preventing or treating systemic fungal infections, it can also be used for prevention and treatment of systemic infections caused by other infectious agents that are sensitive to pimaricin in vivo, such as viruses.

Another aspect of the present invention concerns a method of preparing an antifungal composition for internal use in a mammal, especially a human. This method includes the steps of dissolving pimaricin or an antifungal derivative thereof in a pharmaceutically acceptable dipolar aprotic solvent; and adding to the solution a pharmaceutically acceptable aqueous secondary solvent. In one preferred embodiment, the method further includes the step of lyophilizing the composition, whereby the majority of the water and the aprotic solvent (e.g., more than 50%, preferably more than 95%, and most preferably more than 99% by weight) are removed from the composition and a dry, shelf-stable composition is produced. This dry composition can be reconstituted into an aqueous solution suitable for parenteral administration to a mammal by adding to the dry composition a pharmaceutically acceptable aqueous solvent. Suitable pharmaceutically acceptable aqueous solvents for reconstituting the composition include the known parenteral infusion fluids, such as saline solution and dextrose solution in addition to distilled water.

We have examined the available methods for solubilization and devised nontrivial procedures for solubilizing this agent for parenteral use: we have dissolved it using an organic solvent as the primary vehicle, e.g. dimethylacetamide, and then followed with secondary cosolvents to increase the drug's stable aqueous solubility, or alternatively, we have followed the primary solubilization step with a second aqueous solvent followed by lyophilization to create a pimaricin solvate with minimal organic solvent content, yet one that could be easily reconstituted using distilled water only. Employing a variety of chemical and biological assays we showed that the resulting final pimaricin formulations are stable for several hours at room temperature, and that they retain full antifungal activity. We ultimately used one of the formulations in a canine model to demonstrate that the reformulated pimaricin permits what has heretofore been impossible, namely safe parenteral (e.g., intravascular) administration with negligible toxicity, yielding clearly fungicidal plasma concentrations for more than six hours following the administration.

The present invention provides vehicles for the formulation of pimaricin that are physiologically compatible with parenteral administration in man and domestic animals. The pimaricin formulations of the present invention are non-toxic and can be used for the parenteral treatment of systemic infections sensitive in vitro to this compound, such as infections of Candida, *Aspergillus*, and *Fusarium*, to circumvent the virtually nonexistent intestinal absorption of the drug. The invention will allow the introduction of pimaricin in clinical practice for the therapy of systemic infections, such that the therapeutic outcome for patients with systemic infections sensitive to the drug can be improved.

A high-pressure chromatography technique that allows the accurate determination of low concentrations of pimaricin in various solvent systems and in biological fluids. This patent also describes our in vivo canine model for studying the pharmacokinetics of pimaricin after parenteral administration.

BRIEF DESCRIPTION OF THE DRAWINGS

FIG. 3: HPLC chromatogram of pimaricin in the HPLC assay.

FIG. 9: Pimaricin formulated fresh in DMA/aqueous lipid was assessed for toxicity against the KBM-7/B5 cells (■), and against HL-60 cells (▲), using the MTT assay for 48 hours (FIG. 9a), and for 72 hours (FIG. 9b) as described in materials and methods.

FIG. 10: HPLC chromatograms of a plasma sample analyzed with the HPLC assay.

FIG. 11: Dose linearity of pimaricin utilizing the established HPLC assay in the concentration range 100 ng/ml to 25 µg/ml.

DESCRIPTION OF SPECIFIC EMBODIMENTS

Figure 1:
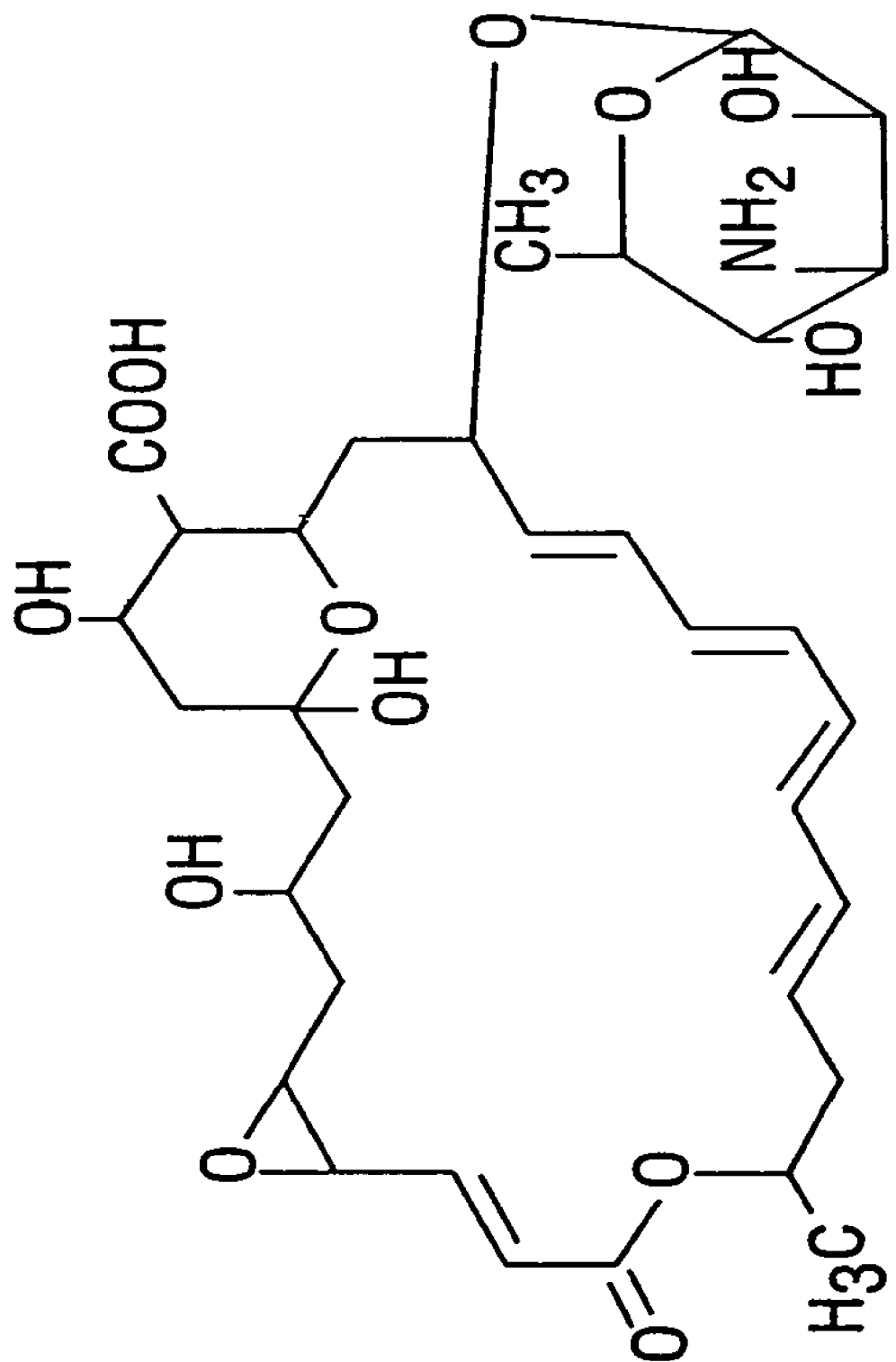
FIG. 1: Chemical structure of pimaricin as free drug.

The following abbreviations are used in this patent:
AMB; Amphotericin B.
ATCC; American Tissue Culture Collection, Rockville, Md.
BMT; bone marrow transplant.
DMA; anhydrous N,N,-dimethylacetamide.
DMF; Dimethylformamide.
DMSO; Dimethylsulfoxide.
FDA; U.S. Food and Drug Administration.
HAc; Glacial acetic acid.
HCl; Hydrochloric acid.
HPLC; High pressure liquid chromatography.
HL-60; Human myeloid leukemia cell line.
IMDM, Iscove's modified Dulbecco Medium (GIBCO, Grand Island, New York, N.Y.).
Intralipid™; Brand name of an aqueous lipid emulsion, made from soy bean oil. and marketed for parenteral nutrition by Clintec.
KBM-7/B5; Human myeloid leukemia cell line.
MeOH; Methanol.
MIC; minimum inhibitory concentration.
MTT; 3,[4,5-dimethylthiazol-2-yl]2,5-diphenyltetrazolium-bromide.
NCI; National Cancer Institute.
NS; Normal saline (150 mM NaCl).
PEG; Polyethylene glycol-400.
PG; Polypropylene glycol/1,2-propylene diol.
RT; Room temperature (22° C.)
SDS; Sodium dodecyl sulphate.

The present invention involves solubilization of pimaricin in pharmaceutically acceptable liquid vehicles, such that the drug remains chemically stable and can be administered intravascularly without undue toxicity from undissolved drug and/or from the solvents at drug doses necessary to obtain clinically significant antibiotic effects.

Pimaricin is available from Gist-Brocades N.V. (Netherlands) and Sigma Chemical Co. (Saint Louis, Mo.). Pimaricin optionally can be used in compositions of the present invention in the form of one of its antifungal derivatives, such as a salt of pimaricin (e.g., an alkali salt or an alkaline earth salt).

We have investigated N,N-dimethylacetamide (DMA), DMSO, glycerol, 1,2,-propylene-diol (PG), and polyethylene glycol-400 (PEG) as primary solvents that would be miscible in secondary solvents, examples of which are normal saline, dextrose in water (5% or 10%), and an aqueous soy bean lipid emulsion (Intralipid™). These solvents are examples of vehicles in which pimaricin could be suitably solubilized, yet be safe for human administration, alone or in combinations with other drugs. The solubility of pimaricin in individual solvent vehicles is shown in Table 1 below.

The described vehicles can be utilized to dissolve pimaricin in concentrations ranging from 1 to more than 100 mg/ml. This range should cover the administration of doses necessary to yield active antibiotic concentrations in vivo that are effective to eradicate systemic infections sensitive to this drug.

The objective of this invention includes the parenteral (e.g., intravascular) administration of pimaricin to improve the control of systemic infections that are sensitive to this agent. As a paradigm for such infections, we will use various molds and other fungal organisms. This use of pimaricin as a parenteral agent has not been previously investigated in the practice of medicine, although the drug has well documented anti-fungal properties in vitro (15–17).

Virtually no pimaricin is absorbed through the intestinal tract after oral administration, making it impossible to even investigate its use as an oral antibiotic against systemic infections. Parenteral administration would therefore be the logical approach to evaluate pimaricin as therapy for deep-seated, systemic fungal infections. Unfortunately, the drug has an exceedingly low solubility in most physiologically acceptable solvents that would be compatible with intravascular administration in man (17).

Our present studies, which are based on the principle of cosolvency (20, 21), show that the composite diluent vehicles we propose for use will solubilize pimaricin without destroying its antifungal properties. Further, the preferred vehicles are nontoxic and safe for administration in large animals (beagles) and should be acceptable for human administration in the proposed concentrations and total doses to be utilized; indeed, DMA, DMSO, and PG have been used for solubilization of various pharmacologically active agents used in man (22–24). The parenteral administration of PEG has been studied in detail in a simian model (25), and PEG has subsequently been used clinically as a (covalently bound) carrier of L-Asparaginase in the treatment of lymphocytic leukemia and lymphoma (26). DMSO is also extensively used as a cryoprotective agent for low-temperature storage of human bone marrow and peripheral blood derived hematopoietic stem cell preparations to be used for transplantation after high-dose chemotherapy (27–30). No serious adverse effects have been experienced from the use of these vehicles. The clinical use of normal saline, dextrose in water (5–70%), and aqueous lipid emulsion are well established means to alter the fluid and electrolyte balance and to supply parenteral nutrition. Normal saline and dextrose in water are extensively used to dilute various medications for parenteral use. However, the aqueous lipid emulsion has not yet found wide-spread use as a pharmaceutical diluent, although this use has been mentioned (31).

The data obtained in our canine model demonstrate that the proposed pimaricin formulations, that is, those that allow parenteral treatment of systemic infections, will provide superior bioavailability. After a one-hour i.v. infusion the plasma concentrations clearly reach, and for an extended time remain in, the fungicidal range as established by our in vitro studies of antifungal activity against *Candida* spp., *Aspergillus* spp., and *Fusarium* spp. Specifically, our novel pimaricin/DMA/lipid solution is chemically stable and simple to handle at RT. It provides reliable and easily controlled dosing with 100% bioavailability. The addition of a lyophilization step virtually eliminates the organic solvent, DMA, from the final clinical "working solution", and it should abolish the potential for adverse reactions related to the DMA, and minimize the possibility for a potentiation of (hepatic) side effects from the combination of DMA and pimaricin. This added step should therefore assist in maximizing patient safety after drug administration.

In cancer patients, the access to parenteral pimaricin will be particularly important, since their intestinal absorption is often perturbed after chemotherapy, aggravating the already erratic intestinal absorption of various medications. The parenteral route will also make it possible to circumvent unpredictable first-pass metabolic effects in the liver, well known to alter the bioavailability of numerous pharmacologically active agents after oral dosing (32). Further, the availability of pimaricin for effective and reliable systemic administration will for the first time make it possible to clinically compare the activity of pimaricin against that of "the gold standard", AMB, for the treatment of systemic mycoses.

In summary, certain infections in immunocompromised patients, e.g. those caused by various molds, particularly *Fusarium*, may be eradicated by pimaricin. In fact, pimaricin may be the only effective drug for the treatment of Fusariosis, since this infection typically is resistant to AMB. The design of a nontoxic, pharmaceutically acceptable, water miscible, parenteral formulation of pimaricin eliminates the risk of treatment failure from the suboptimal bioavailability of oral pimaricin. The addition of a lyophilization step in the preparative procedure will create a pimaricin solvate with minimal DMA content. This will reduce the risk of adverse effects related to the vehicle's organic component.

The following examples are presented to describe the preferred embodiments and utilities of the present invention, but they are not intended to limit the invention to these aspects, unless otherwise stated in the claims appended hereto.

EXAMPLE 1

Pimaricin Formulations Acceptable for Parenteral Administration

The objectives of this experiment were to design formulations of pimaricin that are acceptable for parenteral administration, to calculate the necessary solubility/stability needed to accomplish this goal, and to evaluate our ability to make such preparations with a high pressure liquid chromatographic (HPLC) technique.

Methodology.

Calculation of the Desired Solubility.

We have calculated a relevant solubility range for pimaricin by extrapolation from known values for AMB. AMB is presently the only polyene antibiotic that is FDA-approved for parenteral use. The currently utilized AMB regimens typically prescribe a daily dose of 0.6–1.0 mg/kg body weight as free AMB or 5–6 mg/kg body weight for liposomally-complexed drug (11). We have assumed that a clinically safe maximum infusion rate for pimaricin is 2–3 ml/min over 60–120 minutes, thus arriving at peak plasma concentrations in the range of 3–15 µg/ml (4.5–20 µM). Such concentrations may be necessary if pimaricin treatment is to be successful, since AMB and pimaricin on a molar basis have a similar concentration vs. activity range in vitro (AMB about 0.3–10 µM, and Pimaricin about 3–20 µM). Therefore, the anticipated daily pimaricin dose would be around 1.0–5.0 mg/kg body weight. If this dose were dissolved at a concentration of 1–5 mg/ml, a 50–100-fold increase over the established aqueous solubility of 25–50 µg/ml at RT would be required (17).

Enhanced Solubility in Physiologically Acceptable Solvents.

Pimaricin solubility was determined in several individual vehicles. Briefly, a known amount of the drug, as a powder (different lots of purified drug were obtained from Gist-Brocades N.V., Netherlands, and from Sigma Chemical Company, St. Louis, Mo.), was equilibrated in the respective solvent at RT (22° C.) over 1–4 hours. An aliquot was then removed and diluted in MeOH prior to HPLC at predetermined times. Based on the pimaricin solubility in these particular vehicles, we then attempted to enhance the (stable) solubility by mixing different solvents according to the principle of cosolvency (20, 21). Several different solvent systems were evaluated relative to the above estimates of necessary solubility to arrive at a clinically relevant optimal stock formulation. This stock formula would then be diluted with a "final solvent" to yield the complete working formulation with a pimaricin concentration that could be infused parenterally without problem. For the final solvent we used the commonly utilized parenteral infusion fluids, such as normal saline, dextrose in water (5% or 10%), or a parenterally acceptable aqueous lipid emulsion (e.g. Intralipid™ or Liposyn II™ (Abbott)), all of which are readily available and approved for parenteral administration.

HPLC Assay.

A most accurate and sensitive detection system for low concentrations of pimaricin in solution, both protein-containing and protein-free mixtures, is an HPLC assay utilizing absorbance detection with a variable wave length detector operating in the u.v. spectrum at 293 nm, a value chosen on the basis of the inherent absorption maxima of the pimaricin molecule (17).

We tested this hypothesis using a liquid chromatographic system equipped with an LDC 4000™ multi-solvent delivery system and a Waters™ system 717plus Autoinjector™. The absorbance detector was a LDC 3100 variable wave length detector in sequence with an LDC model CI 4100 fully computerized integrator. The column used was a Whatman EQC™ 10 µl 125A C18 column (4.6 mm i.d.×21.6 cm) (Whatman Inc. Clifton, N.J.). The mobile phase system was an isocratic mixture of MeOH (47% v/v), tetrahydrofuran (2% v/v), and $NH_4$-acetate (0.1% w/v) made up to 100% with double-distilled water. All chemicals were HPLC grade unless otherwise indicated. The flow rate was 1.5 ml/min and the recorder's chart speed was 5 mm/min, modified from (33).

Results and Discussion.

Pimaricin Solubility.

Figure 2:
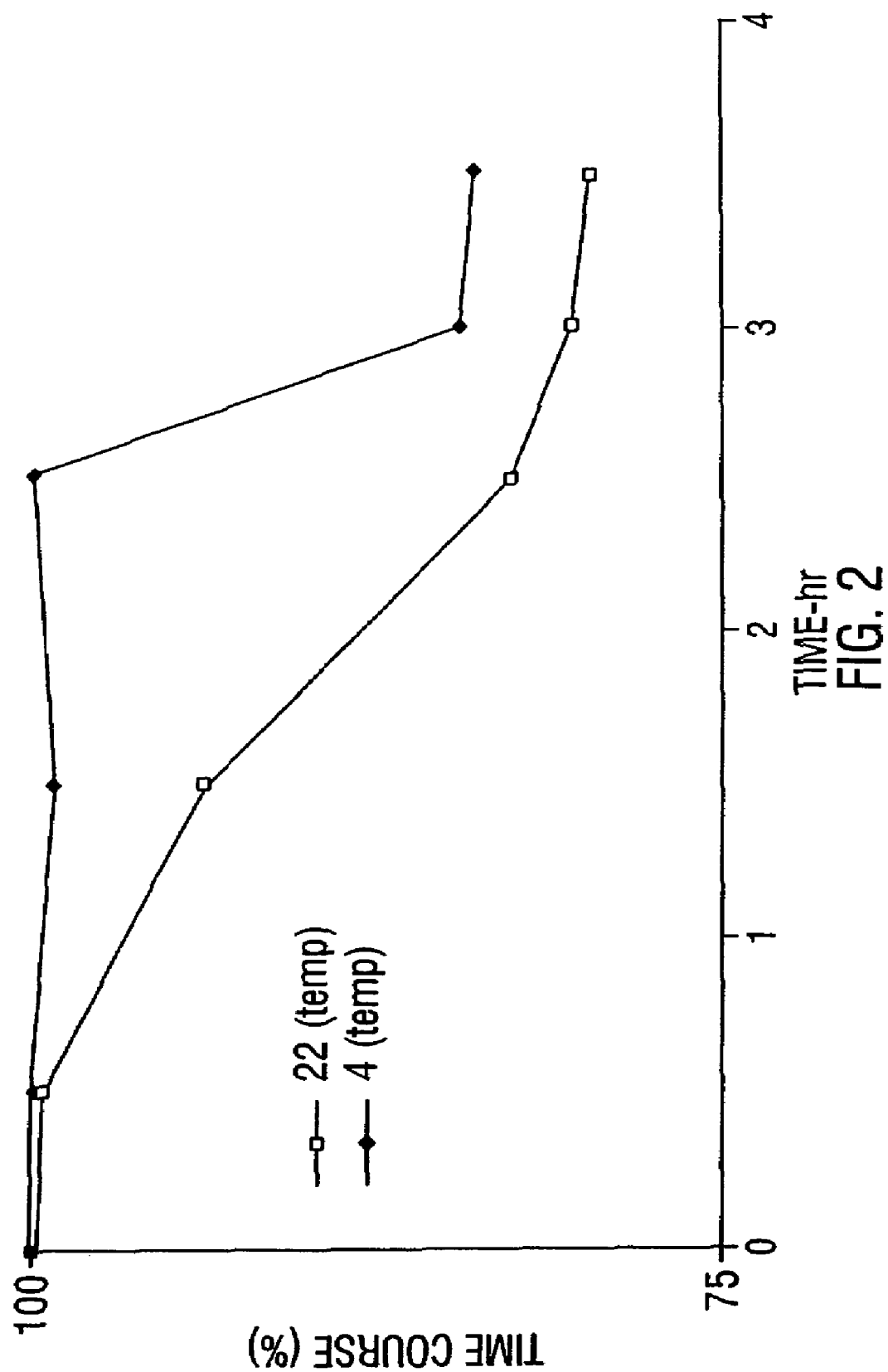
FIG. 2: Stability of pimaricin in DMA alone at 4° C. (♦), and at RT (22° C.) (□), at a concentration of 100 mg/ml. The y-axis shows the fraction of drug remaining as percentage of control (i.e, starting concentration).

Several strategies were evaluated to solubilize pimaricin in water-miscible physiologically acceptable vehicles that would be compatible with human administration. The examined candidate solvents included castor oil, DMA, DMSO, PEG, and PG, in addition to the aqueous solvents HAc, NS, 5% dextrose in water and an aqueous soy bean emulsion (Intralipid™). HAc and DMA were the best primary solvents, followed by DMSO, whereas pimaricin as expected was insoluble in most of the aqueous solvents. Only with HAc and DMA did we reach a solubility in excess of 10 mg/ml. Further, although pimaricin could be dissolved in HAc and DMA to at least 100 mg/ml, it started degrading already within a few hours in solution (FIG. 2). Stabilizing the pimaricin once dissolved in DMA was then addressed with a cosolvency approach (20, 21). Numerous cosolvent combinations were investigated; the composite organic system of DMA/DMSO/PEG/PG appeared to work well, but it did still only allow pimaricin to be dissolved at a final concentration of about 10 mg/ml. This composite vehicle did not allow stable solubilization of pimaricin for more than a few hours. When NS or 5% dextrose in water was added, significant degradation rapidly took place. In contrast, a different pattern was recorded when a lipid-containing cosolvent was utilized. When HAc was used as the primary solvent, the best secondary solvents appeared to be DMA, DMSO or Intralipid™.

HPLC Assay.

Figure 3A:
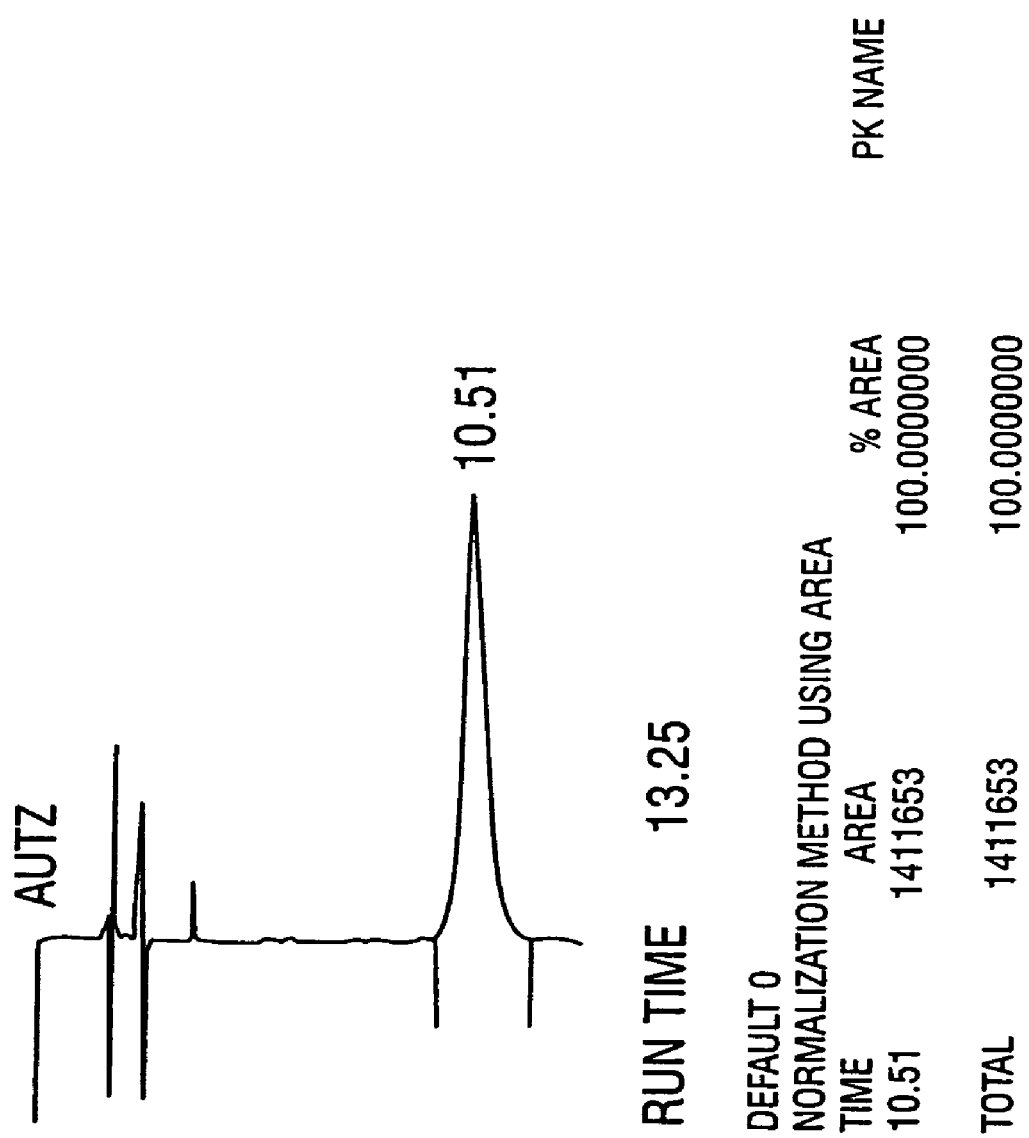
FIG. 3a: Pimaricin extracted from an aqueous solution of 5 μg/ml.
Figure 3B:
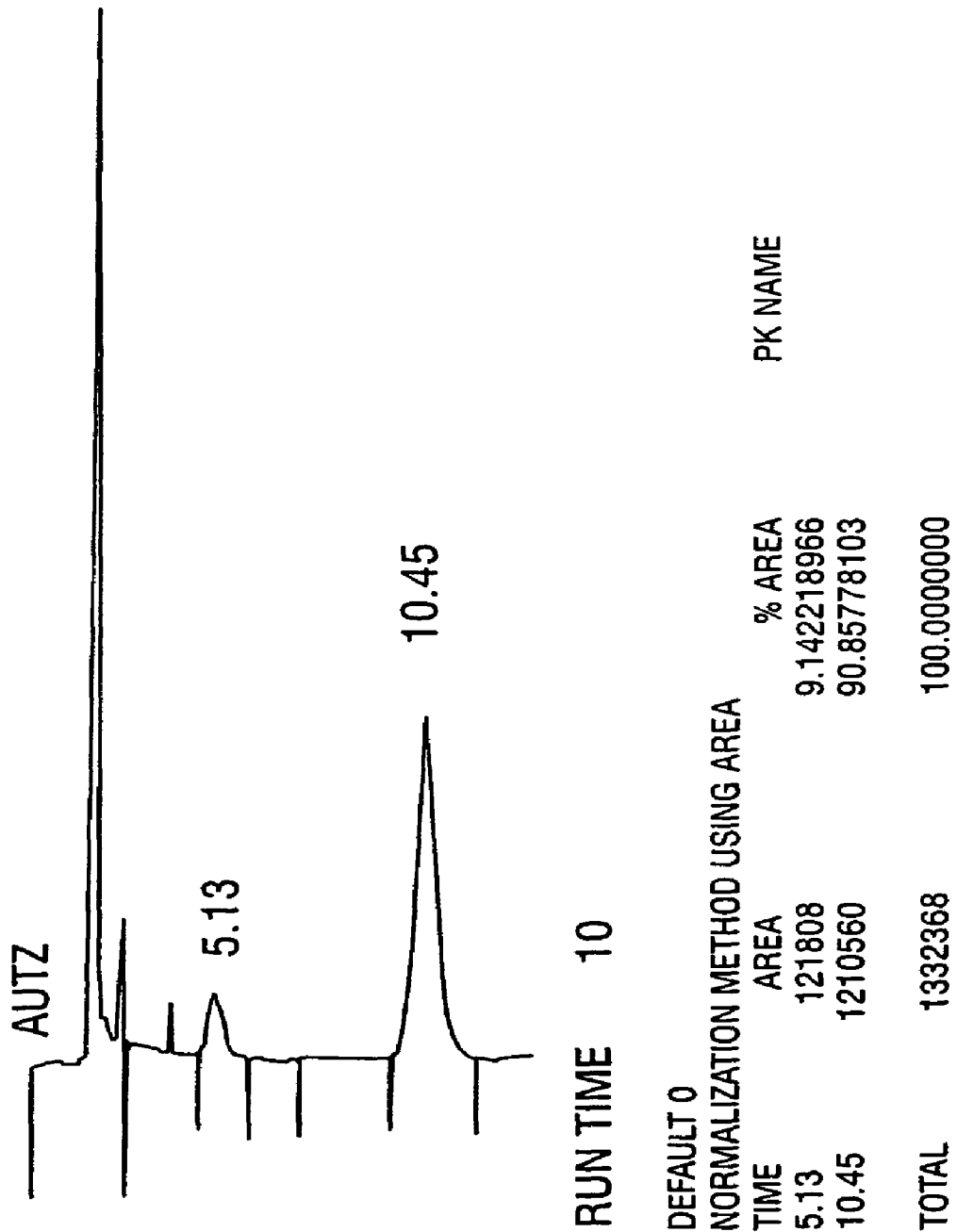
FIG. 3b: Pimaricin extracted from a plasma sample spiked to a concentration of 5 μ/ml.

Two examples of pimaricin chromatograms from the HPLC assay are shown in FIG. 3. In FIG. 3a the drug was analyzed in the aqueous DMA-Intralipid solvent, and in FIG. 3b it was extracted from human plasma that had been spiked with 5 µg/ml prior to is extraction as described above. The retention time under the above conditions was 9.8–10.8 min, and the assay was linear from 100 ng/ml to 25 µg/ml in protein-free solutions, i.e. the various solvent systems utilized in the formulation-feasibility and -stability studies, and from about 50 ng/ml to 1 mg/ml for protein-containing solutions (plasma samples). This assay consistently yielded high recovery, accuracy and a lower sensitivity limit of about 10 ng/ml. The technique was standardized and used without modifications for the studies of both stability and pharmacokinetics.

EXAMPLE 2

Solubility and Stability Studies of Various Formulations

The objectives of this experiment were to: (1) design stable pimaricin formulations that are suitable for parenteral administration; (2) establish the chemical and physical stability of pimaricin in the novel vehicles: (3) establish the solubility of pimaricin in these vehicles when mixed with NS. dextrose in water, and Intralipid™; and (4) investigate the in vitro properties of these formulations: i.e. their osmolarity, hemolytic potential, and cytotoxicity, to show that they are appropriate for the intended purpose.

Methodology.

Solubility Studies.

An excess amount of pimaricin as a solid powder was added to castor oil, DMA, DMSO, PEG, and PG at RT. Each mixture was placed in a dark environment and checked visually for up to 4 hours for evidence of solubilization. Samples of 1 ml were taken at various time intervals, and filtered through a 0.45 µm PTFE membrane filter fitted to a syringe assembly (Whatman Inc.), and after appropriate dilution, the pimaricin concentration was determined by HPLC.

Stability of the Various Pimaricin Formulations.

To study the physical and chemical stability of the various parenteral formulations, three sets of experiments were performed:

(a) Pimaricin was dissolved at a concentration of 100 mg/ml in DMA ("stock solution") and incubated at 4° C., at 22° C. and at 40° C. We analyzed the drug concentration by HPLC in samples taken immediately after solubilization and after is gradually increasing time intervals of up to 48 hours.

(b) The pimaricin-DMA stock solution was diluted with PEG/water (1:1:1, v:v:v, DMA:PEG:water), or PG/DMSO (1:1:1, v:v:v), or PG/DMSO/PEG (1:1:1:1, v:v:v:v), or aqueous lipid emulsion (1:10 and 1:100, v:v, DMA:Intralipid™), to yield pimaricin concentrations ranging from 1–10 mg/ml.

(c) The DMA-pimaricin mixture was diluted in NS or 5% dextrose to a drug concentration of 1 mg/ml.

(d) The pimaricin-HAc mixture was blended with DMSO and Intralipid™ or directly in Intralipid™.

The various formulations were analyzed by HPLC immediately after mixing, then hourly for 8 hours, and then at gradually increasing time intervals up to several weeks, depending on the rate of degradation in the respective solvent system.

The solubility of the drug differed markedly between different solvents (Table 1). Only DMA and HAc, which provided the highest solubility were considered for extended studies as primary solvents.

TABLE 1

Solvents Tested for Solubilization of Pimaricin

| Formulation | Time Allowed to Solubilize (hr) | Maximum Solubility (mg/ml) | Vehicle |
|---|---|---|---|
| 1 | 4 | 2 | DMSO |
| 2 | 4 | 10 | DMA |
| 3 | 6 | 100 | DMA |
| 4 | 4 | 0.078 | PG |
| 5 | <0.2 | >300 | HAc |
| 6 | 4 | N/S | Castor oil |
| 7 | 4 | N/S | PEG400 |
| 8 | 4 | N/S | Intralipid |

(N/S indicates that pimaricin was not soluble in that solvent.)

To lower the DMA concentration in the final stock- and use-formulations without adversely affecting the drug's shelf life, we investigated lyophilization as part of the preparation of a complete pimaricin/DMA/aqueous lipid-solvate vehicle.

Osmotic Pressure Measurement.

Osmotic pressures were measured with a micro-osmometer model 3MOplus osmometer (Advanced Instruments Inc., Needham Heights, Mass.). The instrument was calibrated using Advans™ intrinsic calibration standards (Advanced Instruments Inc.) over a range of 500–2000 mOsm/kg. The test solution was placed in a disposable cuvette from the test kit, and the osmotic pressure readings were recorded after equilibration in units of mOsm/kg. Triplicate measurements were carried out for each vehicle (without pimaricin), and six measurements were done with pimaricin added.

We used a two-tailed t-test to evaluate the differences in osmotic pressures of the various vehicle formulations with and without the addition of pimaricin (34). The difference between the means of the two groups was to be considered significantly different for $P \leq 0.05$.

Hemolysis Studies in vitro.

We employed the procedure of Parthasarathy et al to examine the hemolytic potential of a few selected preparations (35), and the $LD_{50}$ values of the various formulations were constructed as described. Briefly, heparinized blood was mixed with an equal volume of Alsever's solution. This mixture was washed twice in PBS, and a 10% (v/v) erythrdcyte/PBS solution was then prepared and mixed with increasing amounts of the complete solvent system with or without the addition of pimaricin. These mixtures were then incubated for 4 hours at 37° C. At the end of the incubation, the cells were pelleted at 10,000×g in an Eppendorff™ centrifuge, and the release of hemoglobin in the supernatant (i.e. hemolysis) was spectrophotometrically determined at 550 nm. Maximum lysis was measured against a reference solution of erythrocytes that had been completely lysed by hypotonic shock. The hemolytic potential of three of the complete formulations was evaluated as described (35), and the data were plotted as the fraction of healthy cells versus In (natural logarithm) (total volume percent). Total volume percent was defined as the volume percent of the vehicle in the mixture after dilution with blood. This was done in an attempt to simulate the dilution of the respective drug formulation in the bloodstream after parenteral administration. Healthy erythrocytes were defined as those capable of retaining their hemoglobin intracellularly after mixture with the various pimaricin formulations (35).

In Vitro Cytotoxicity of Pimaricin.

The cytotoxic potential of selected solvent systems with and without pimaricin was determined against the two human myeloid leukemia cell lines HL-60 (36) and KBM-7/B5 (37, 38), using a modification of the previously published MTT assay (39, 40). Briefly, HL-60 or KBM-7/B5 cells in Iscove's modified Dulbecco medium (IMDM) supplemented with 10% fetal bovine serum were incubated for 60 min at 37° C. with the complete vehicles (a: DMA/PG/DMSO/PEG in ratios 1:1:1:1, v/v, and b: DMA/Intralipid™, 1:10, v/v, or c: HAc/DMSO/Intralipid™, 2:6:3, v/v) at increasing concentrations of the vehicle (0.5%, 1.0%, 2.0%, 3.0%, and 10%, v/v) with or without pimaricin. At the end of the 60 min incubation the cells were washed in ice-cold PBS and resuspended in IMDM with 10% fetal bovine serum at 37° C. Twenty-four hours later 25 µl MTT solution (5 mg/ml) (Sigma Chemicals, St. Louis, Mo.) was added to each sample, and following an additional 2 hours of incubation at 37° C., 100 µl extraction buffer was added [extraction buffer: 20% (w/v) SDS dissolved to saturation at 37° C. in a solution of DMF and deionized water (1:1); pH 4.7]. After incubation overnight at 37° C., the optical densities were measured at 570 nm using a Titer-Tech™ 96-well multi-scanner™, against extraction buffer as the calibrating blank. The cytotoxicity was determined as the colorimetric difference between the samples exposed to solvent±pimaricin as above and the background reactivity of cells that had been incubated in parallel in PBS alone. All determinations were performed in triplicate (39, 40).

Results and Discussion.

Equilibrium Solubility Determinations and Stability Studies in Various Solvent Vehicles.

A maximum equilibrium solubility of pimaricin of >100 mg/ml was achieved in DMA after 4 hours at RT. The drug formulations in castor oil, DMSO, PEG-400 and PG achieved considerably lower equilibrium concentrations (Table 1). The latter solvents neither provided an acceptable solubility nor chemical stability of the dissolved drug, and these vehicles were therefore not considered for further studies. Once a pimaricin solubility of 100 mg/ml was reached in anhydrous DMA and HAc respectively, the drug started degrading with a loss of approximately 5–10% over the subsequent 3–4 hours. The drug was more stable when PEG was used as a secondary solvent, but again drug degradation began within another few hours at RT. At 4° C. the drug was more stable, but degradation was still apparent within 8 to 12 hours.

The temperature-dependent stability of solubilized pimaricin in the different1 solvent systems was studied as follows: The drug was dissolved in DMA at 100 mg/ml, and different aliquots were stored at 4° C. at 22° C., and at 40° C. Immediately after solubilization and at various intervals up to 48 hrs later, aliquots from the different samples were analyzed by HPLC. The drug samples stored at 4° C. and at 22° C. degraded slower than those stored at higher temperatures: at 40° C. the pimaricin started degrading within 1 hour after the start of incubation, and at RT there was a loss of 5–10% in the first four hours.

Figure 4:
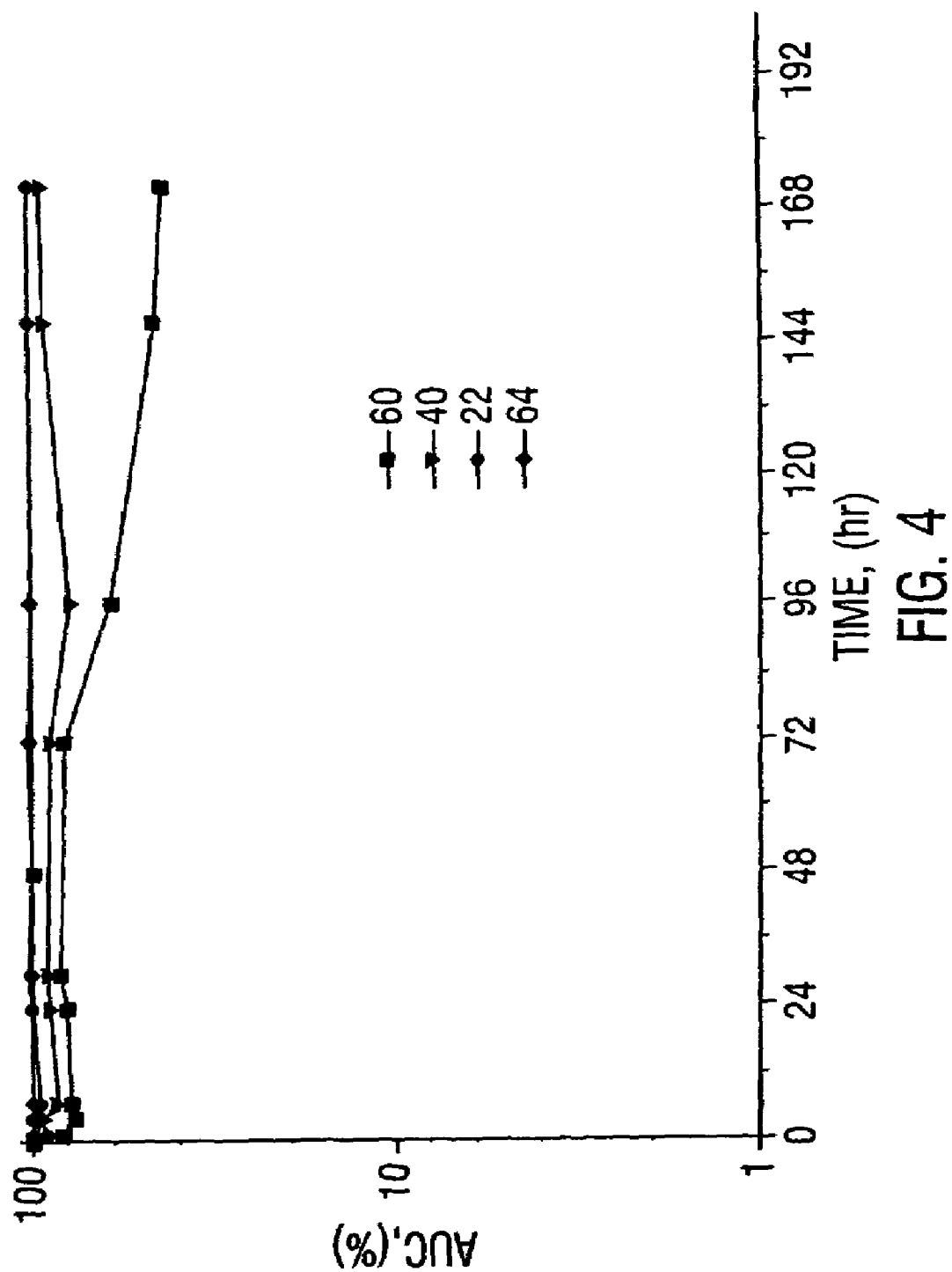
FIG. 4: Stability of pimaricin at 4° C. 22° C., 40° C., and 60° C. The pimaricin formulation was in DMA-aqueous lipid emulsion prepared "fresh," "AUC" is the area under the curve of the pimaricin peak in the chromatogram. This represents drug concentration, but in this experiment it was not translated into a numerical drug concentration using a standard curve plotting AUC vs. drug concentration.

When the 20% aqueous lipid emulsion (Intralipid™) was used as a secondary solvent, a different stability pattern was recorded; when the pimaricin concentration was adjusted to 1–10 mg/ml by dilution with 20% Intralipid of the DMA-pimaricin and the HAc-pimaricin stock solutions, the drug was stable for more than 7 days (FIG. 4).

The major fraction of the organic solvent, DMA, was removed by lyophilization of the pimaricin/DMA/aqueous lipid complex to create a solvate that was stable yet easily reconstituted by adding only double-distilled water under gentle agitation without any appreciable loss of anti-fungal efficacy. Indeed, within a few minutes after addition of distilled water to the solvate, the drug was reconstituted at 1–10 mg/ml, with only trace amounts of the organic solvent remaining. This reconstituted pimaricin formulation retained an anti-fungal efficacy that was equivalent to that of the freshly prepared DMA/aqueous lipid formulation when assayed in vitro (see below under Example 3). This reconstituted formulation was also stable at 4° C. for more than 2 weeks. The lyophilized pimaricin formulation remained stable (by HPLC) for more than four months at 4° C. This preparation could still be readily reconstituted to 10 mg/ml within a few minutes with distilled water, with retention of full anti-fungal activity in vitro (see Tables 3 and 4 below).

Figure 5:
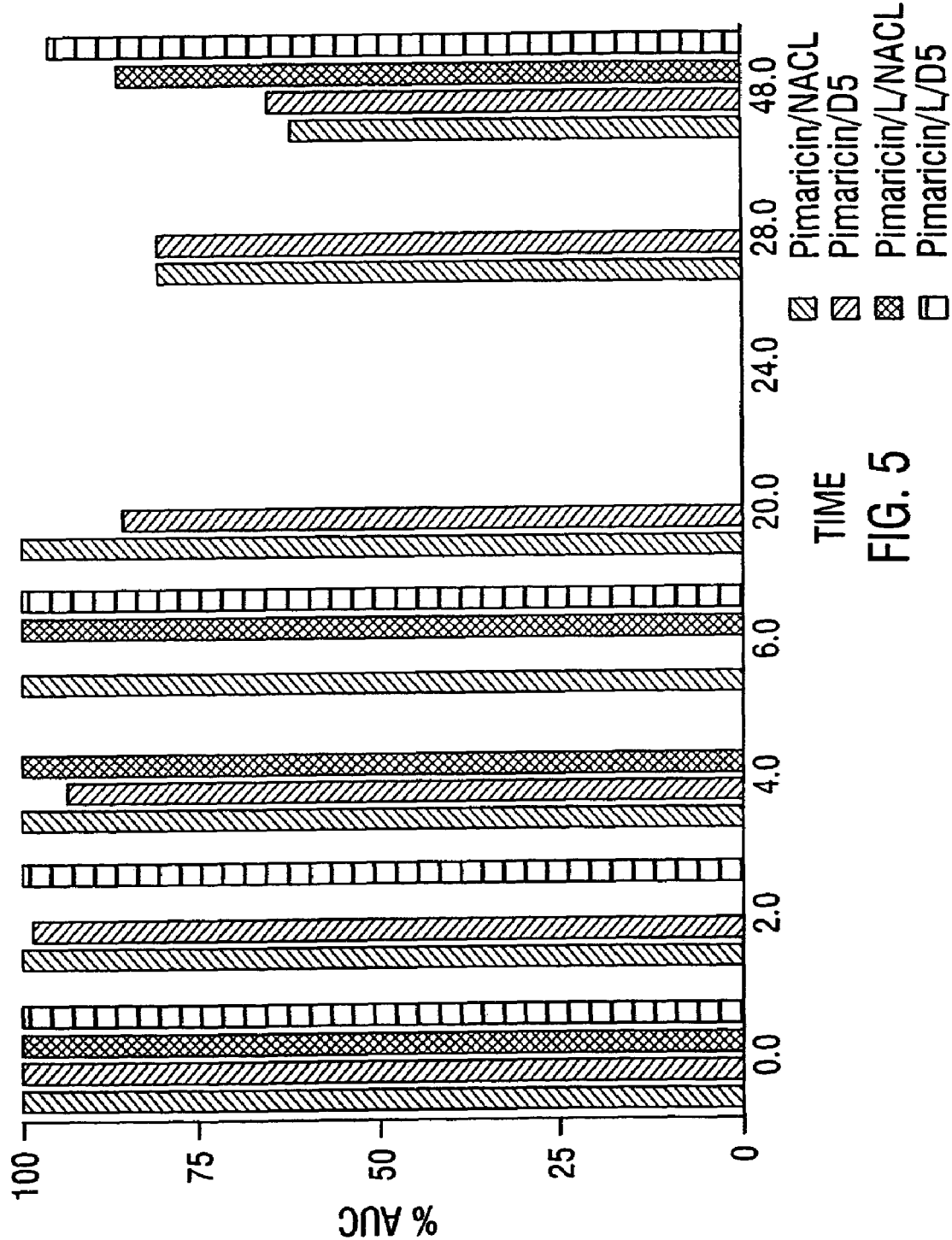
FIG. 5: Stability over 48 hours of the final solution for clinical use, maintained at RT after dilution to 1 mg/ml. The symbols refer to the following solutions: Pimaricin/L/NACL: the lyophilized and reconstituted solution was diluted from 10 mg/ml to 1 mg/ml with NS. Pimaricin/L/D5: as above, but the secondary solvent was 5% dextrose instead of NS. Pimaricin/NACL: the DMA/Intralipid™ formulation was prepared fresh to a concentration of 10 mg/ml as described, and the secondary solvent used was NS. Pimaricin/D5: The same DMA/Intralipid™ formulation as above, prepared fresh, but the secondary solvent was 5% dextrose instead of NS.

We further simulated a final clinical use-formulation with a pimaricin solution of 1 mg/ml by diluting the 10 mg/ml-formulations (prepared fresh with DMA/Intralipid or after lyophilization/reconstitution respectively) with 5% dextrose or NS. FIG. 5 shows the respective stability at RT of these "use-formulations". Similarly, when HAc and DMSO were used as the primary solvent system prior to mixing with Intralipid and followed by lyophilization, the majority of the organic solvent, here DMSO, was removed and the result was a stable lipid-based solvate, that could be easily reconstituted to 10 mg/ml under gentle agitation after the addition of distilled water. This reconstituted formulation was also stable for more than 24 hours at RT assessed by HPLC.

Osmotic Pressure.

It is desirable that a parenteral formulation of a pharmacologically active agent be isosmotic to blood. A hypertonic delivery system can be utilized if the drug/solvent is infused through a (central) venous catheter and gradually diluted in a large blood volume. The osmotic pressure of the various formulations is shown in Table 2.

TABLE 2

Osmotic Pressures of Various Vehicles with and without Pimaricin

| Solution | n | Osmotic pressure mOsm/kg |
|---|---|---|
| Water | 3 | 3 |
| Normal saline | 3 | 233 |
| 5% dextrose in water | 3 | 286 |
| Blood, human | 6 | 280–295 |
| DMA:PEG:PG | 3 | 4492 |
| Pimaricin in DMA:PEG:PG | 3 | 4732 |
| Intralipid | 3 | 340 |
| DMA:Intralipid (1:10, v/v) | 3 | 2067 |
| Pimaricin in DMA:Intralipid (1:10, v/v, fresh) | 3 | 1930 |
| DMA:Intralipid (1:10, lyophil.-reconstit.) | 3 | 157 |
| Pimaricin (1 mg/ml) in DMA:Intralipid (1:10, lyophil.-reconstit.) | 3 | 208 |
| Pimaricin (25 mg/ml) in DMA:Intralipid (1:10, lyophil.-reconstit.) | 3 | 243 |

(n represents the number of independent determinations.)

The DMA-stock formulation with or without pimaricin was very hypertonic; its osmotic pressure was more than 1,900 mOsm/kg, as compared with 280–295 mOsm/Kg for human blood. The DMA/PG/DMSO/PEG and DMA/PEG solvents were almost as hypertonic. In contrast, the DMA/Intralipid preparation was closer to isosmotic when reconstituted after lyophilization. Similarly, the lyophilized/reconstituted HAc/DMSO/Intralipid™ vehicle was also close to isosmotic. Adding pimaricin to the respective vehicles did not appreciably change their osmolarity (P>0.05).

Hemolysis.

Figure 6:
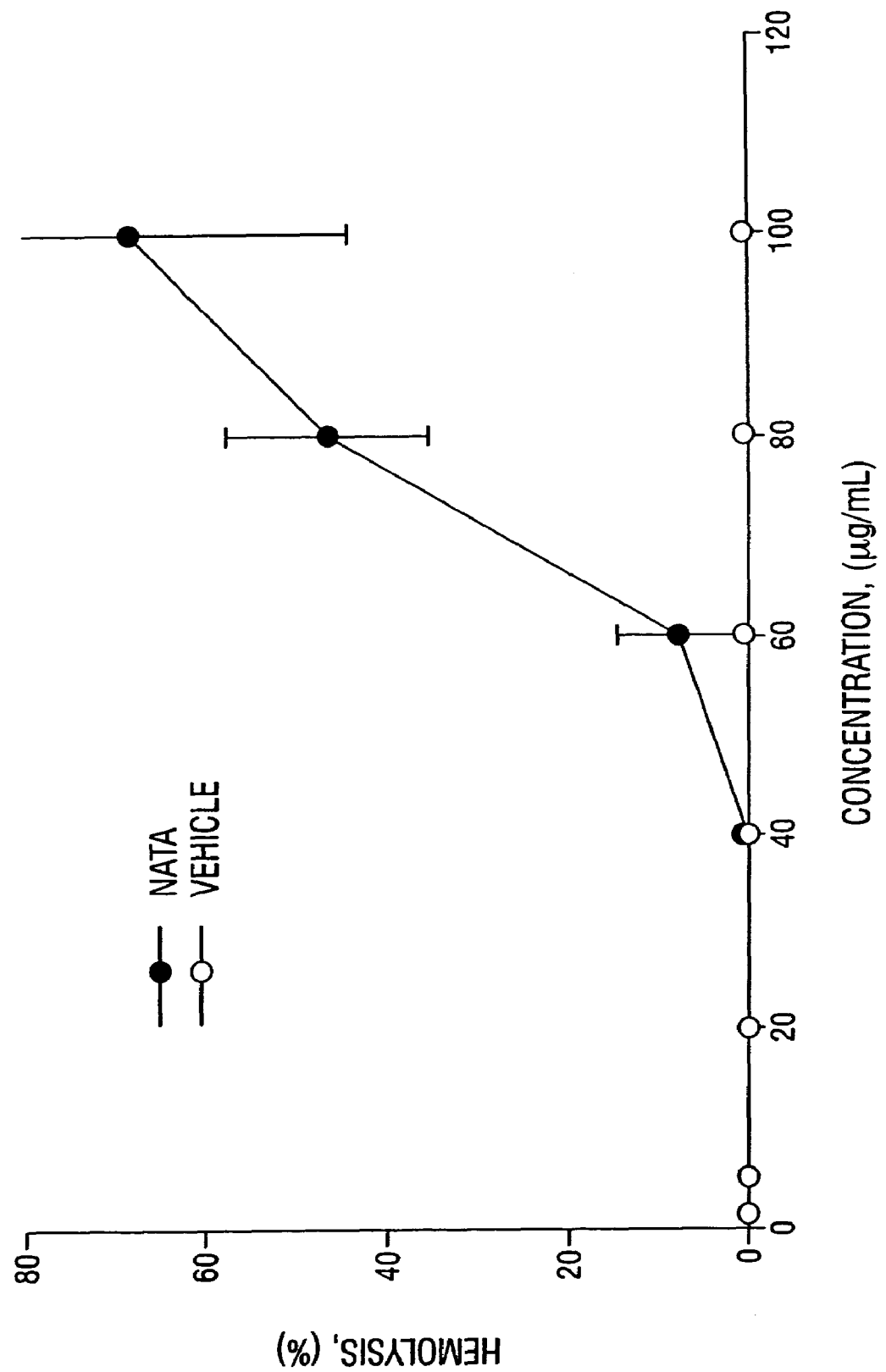
FIG. 6: Hemolytic effects of the DMA/DMSO/PEG/PG formulation without (○) and with pimaricin (●).
Figure 7:
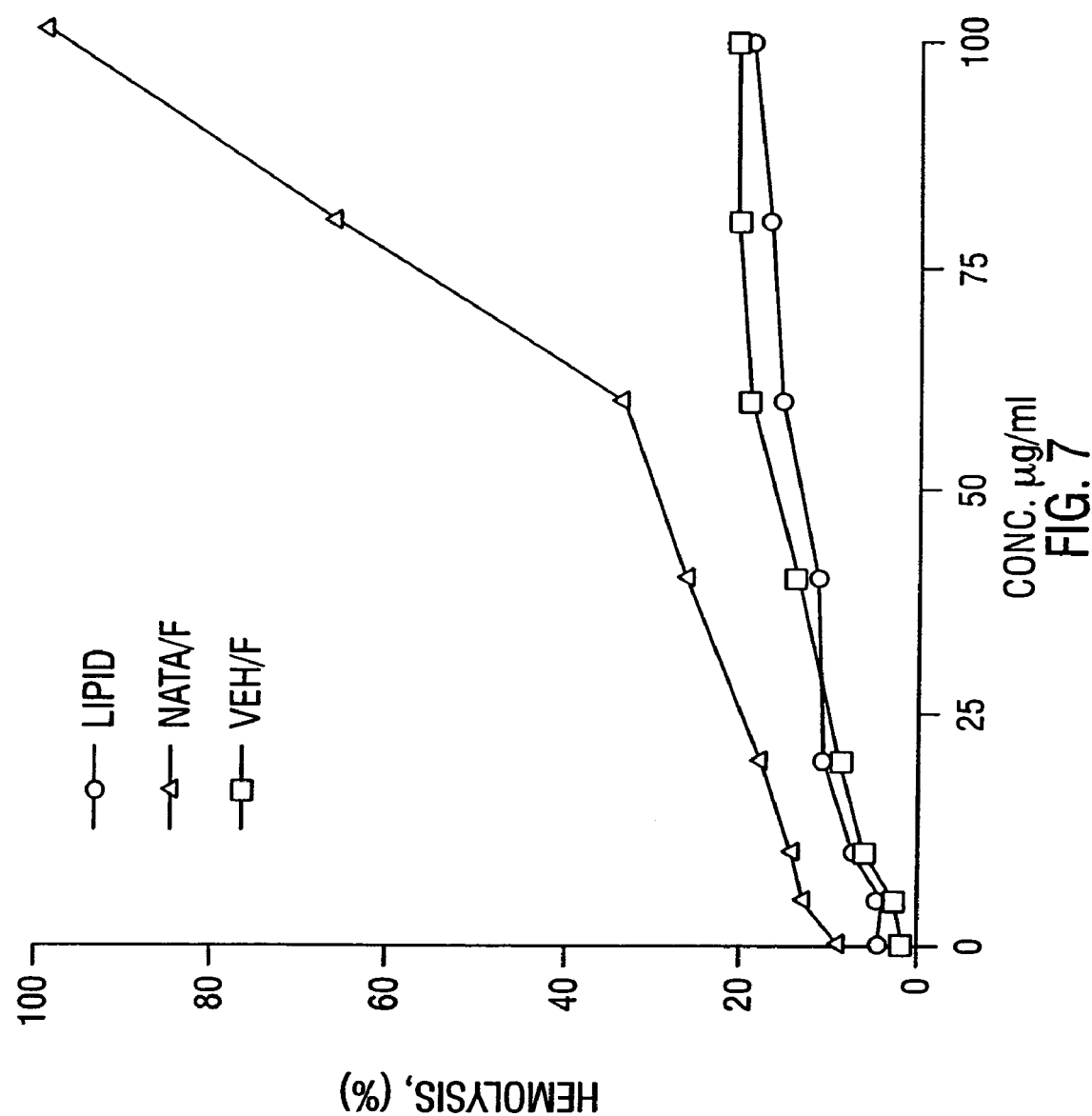
FIG. 7: Hemolytic effect of the freshly prepared DMA/aqueous lipid formulation without (□) and with pimaricin (Δ). Negative control was 10% aqueous lipid (Intralipid™) alone (○), at a concentration comparable to that when pimaricin was added to the vehicle at the concentration indicated on the abscissa.
Figure 8:
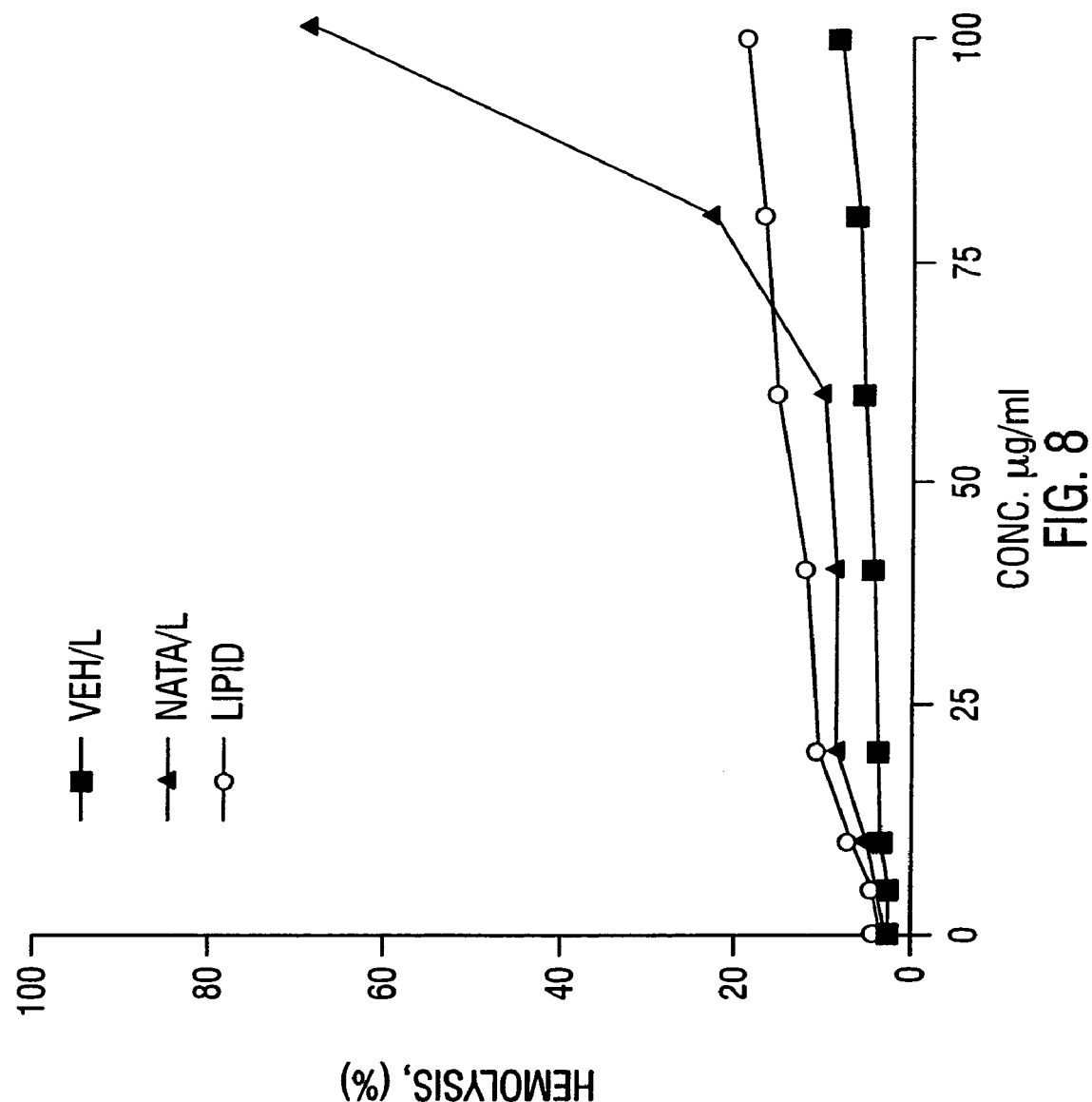
FIG. 8: Hemolytic effect of the DMA/aqueous lipid solution lyophilized and reconstituted in double-distilled water without (■) and with pimaricin (▲). Negative control was the 10% aqueous lipid (Intralipid™) alone (○), at a concentration comparable to that when pimaricin was added to the vehicle at the concentration indicated on the abscissa.

As shown in FIGS. 6–8, the formulations studied showed similar trends for hemolysis with the addition of pimaricin. The pimaricin dependent lysis was notable at concentrations exceeding 40 μg/ml for the composite organic solvent and at ≧50 μg/ml for the freshly prepared DMA/Intralipid formulation and at ≧60 μg/ml for the lyophilized-reconstituted DMA/aqueous lipid formulation. The drug-specific hemolysis was highly reproducible between different experiments, as was the internal ranking between the various solvent systems between the different experiments. The detailed data for the different vehicles with and without pimaricin are summarized in FIGS. 6–8. $LD_{50}$ values can be deduced from this information. The DMA/Intralipid™ "fresh" formulation had a significantly lower hemolytic potential than the DMA/PEG/PG/DMSO composite organic vehicle. Further, the hemolytic potential of the lyophilized DMA/Intralipid formulation was significantly lower than that of the freshly prepared DMA/aqueous lipid formulation for all pimaricin concentrations from 1 μg/ml up to 100 μg/ml. Finally, pimaricin-induced hemolysis in all of the tested vehicles was significantly lower (>10-fold) than that observed for various AMB formulations ($LD_{50}$ values in the range of about 4–5 μg/ml) under similar experimental conditions (41).

In Vitro Cytotoxicity of Pimaricin.

The HL-60 and KBM-7/B5 myeloid cells were exposed to the selected vehicles at increasing volume ratios with or without the addition of increasing drug concentrations. The cytotoxicity of each formulation was then assayed in the MTT assay (39, 40). None of the examined solvent systems exerted any detectable toxicity against the cells in this assay (FIG. 9).

EXAMPLE 3

Antifungal Activity of Solubilized Pimaricin

The objective of this experiment was to critically evaluate the in vitro antifungal activity of pimaricin when solubilized in a few selected vehicles using solution AMB as the reference solution.

Methodology.

The antifungal activity of pimaricin was compared with that of amphotericin B utilizing a previously described assay (42). Briefly, serial dilutions of pimaricin and AMB were mixed in RPMI growth medium with L-glutamine and MOPS-buffer. pH 7.0 (Sigma Chemical Co., St. Louis, Mo.). The different strains of *Candida*, *Aspergillus* and *Fusarium* spp. were then added to the dishes. After incubation at 35° C. for 48–72 hours the plates were evaluated for fungal proliferation. The used fungal strains were obtained from the ATCC or isolated from patients, primarily at the MD Anderson Cancer Center. The pimaricin concentrations in the used solutions were assayed in parallel with HPLC to assure the highest possible reproducibility of the drug concentrations.

Results and Discussion.

The sensitivity data are displayed in Tables 3 and 4.

TABLE 3

Sensitivity of Fungal Organisms Against Various Pimaricin Formulations

| Organism | Code | L/D μg/ml | Rm-temp μg/ml | F/D (nata + lipid) μg/ml |
| --- | --- | --- | --- | --- |
| *Aspergillus fumigatus* | 6-2535 | 2 | 2 | 2 |
| *Aspergillus fumigatus* | 6-7784 | 2 | 2 | 2 |

TABLE 3-continued

Sensitivity of Fungal Organisms Against Various Pimaricin Formulations

| Organism | Code | L/D μg/ml | Rm-temp μg/ml | F/D (nata + lipid) μg/ml |
| --- | --- | --- | --- | --- |
| *Aspergillus niger* | 6-2165 | 2 | 2 | 2 |
| *Aspergillus fumigatus* | 6-5337-1 | 2 | 2 | 2 |
| *Fusarium moniliformi* | M6306 | 2 | 2 | 2 |
| *Aspergillus flavus* | 6-4594-2 | >16 | >16 | >16 |
| *Fusarium solanii* | s-1184 | 2 | 2 | 2 |
| *Candida albicans* | ATCC 64545 | 2 | 2 | 2 |

The organisms of Table 3 were prepared as specified in the methodology in Example 3. "L/D" refers to a formulation where pimaricin was dissolved to 100 mg/ml in DMA, then diluted to 10 mg/ml with 20% Intralipid, lyophilized and then stored for >4 months at 4° C., followed by reconstitution in normal saline to 10 μg/ml as "use-solution". "Rm-temp" refers to a formulation where pimaricin was prepared fresh in DMA and Intralipid (10 mg/ml), kept for one week at RT, and then tested for its antifungal properties. "F/D (Nata+lipid)" refers to a formulation where pimaricin was freshly dissolved at 100 mg/ml in DMA and then diluted with 20% Intralipid to 10 mg/ml as a fresh use-solution that was diluted to final concentrations of <2 to 16 μg/ml as described herein.

Table 4 reports the results of another similar experiment.

TABLE 4

Sensitivity of Fungal Organisms Against Various Pimaricin Formulations

| Organism | Code | Lipid + DMA (1:10) μg/ml | Nata-lipid 1 μ/ml | Nata-lipid 2 μg/ml | AMP + DMSO μg/ml |
| --- | --- | --- | --- | --- | --- |
| *Aspergillus fumigatus* | 6-2535 | >16 | 2 | 2 | 0.125 |
| *Aspergillus fumigatus* | 6-7784 | >16 | 2 | 2 | 0.25 |
| *Aspergillus niger* | 6-2165 | >16 | 2 | 2 | 0.03 |
| *Aspergillus fumigatus* | 6-5337-1 | >16 | 4 | 4 | 0.5 |
| *Aspergillus flavus* | 6-4594-2 | >16 | >16 | >16 | 1 |
| *Aspergillus fumigatus* | 6-209 | >16 | 2 | 2 | 0.25 |
| *Aspergillus fumigatus* | 6-0960 | >16 | 2 | 2 | 0.25 |
| *Aspergillus fumigatus* | 6-1886 | >16 | 4 | 4 | 0.25 |
| *Aspergillus fumigatus* | 6-1261 | >16 | 4 | 4 | 0.25 |
| *Aspergillus flavus* | 4-9044 | >16 | >16 | >16 | 1 |
| *Aspergillus flavus* | 6-5337-2 | >16 | >16 | >16 | 1 |

"Lipid+DMA" refers to freshly mixed DMA and Intralipid (1:10, v/v), which exerts no antifungal activity by itself. For "Nata-lipid 1" and "Nata-lipid 2, " pimaricin was dissolved in DMA to 100 mg/ml then diluted with 20% Intralipid to 10 mg/ml "use-formulation." "Nata-lipid 1" refers to a formulation where pimaricin was dissolved as above, and after dilution to 10 mg/ml using Intralipid, it was lyophilized. The lyophilized material was refrigerated for 4 months, then reconstituted in normal saline to 10 mg/ml and tested for antifungal activity. "Nata-lipid 2" refers to a formulation where the pimaricin/DMA/Intralipid formulation was prepared as for Nata-lipid 1 and lyophilized immediately, and was reconstituted and tested for antifungal activity three days later. "AMP+DMSO" refers to a formulation of Amphotericin B dissolved immediately prior to use in DMSO, to serve as a positive control.

The activity of pimaricin was similar to that of AMB. Most of the *Aspergillus* and *Fusarium* spp. were sensitive to pimaricin, independent of the solvent system. Importantly, the DMA/Intralipid™ formulation that was lyophilized and reconstituted with distilled water only, retained full and stable anti-fungal efficacy, when assayed both after 3 days and after more than 4 months at 4° C. All the *Aspergillus* strains, except for A. flavus, had pimaricin MIC values in the 2–4 μg/ml (2.1–4.2 μM) range. The tested A. flavus was also sensitive to the drug, but with a slightly higher MIC value of 16 μg/ml (17 μM). All the tested strains of *Fusarium* and *Candida* spp. were sensitive to pimaricin in the range of 2–4 μg/ml (Tables 2 and 3).

EXAMPLE 4

Quantitative Pimaricin Analysis in Plasma and Pharmacokinetics of iv Pimaricin

The objective of this experiment were:

(1) To show that the drug can be administered intravenously and recovered from the plasma from experimental animals using a quantitative extraction technique and HPLC assay; and (2) To show that the pimaricin plasma pharmacokinetics after iv administration of the DMA/20% aqueous lipid formulation in beagle dogs are appropriate for treating systemic microbial diseases, in particular Fusariosis.

Methodology.

Quantitative Extraction of Pimaricin in Plasma.

Canine plasma (0.2 ml) and human plasma (0.5 ml) were mixed with various amounts of pimaricin (in <3% of the final volume), to yield a drug concentration of 0.05–3.0 μg/ml (from a pimaricin stock solution in DMA/20% Intralipid™ at a concentration of 10 mg/ml). The drug was extracted from plasma samples using a slight modification of the method described by Napoli et al (43). Briefly, 0.2 ml plasma was mixed with 0.2 N HCl in MeOH (1:1, v/v), and after thorough mixing by a vortex machine, the sample was extracted with three volumes of hexane. The hexane was separated from the pimaricin by evaporation and the drug was reconstituted in 200 μl of MeOH prior to HPLC (43). Pimaricin was spectrophotometrically detected in the HPLC analysis as described above on page 14. The pimaricin recovery from human plasma spiked to a pimaricin concentration of 10 μg/ml was calculated to be 91±5%, and from canine plasma it was estimated to be in the order of 85±4%. The assay was linear in the interval from 50 ng/ml to at least 1,000 μg/ml.

Parenteral Pimaricin in Beagles: Experimental Protocol.

For the pharmacokinetics experiment we elected to use beagle dogs, since these animals are exceedingly sensitive to the toxic adverse effects of polyene antibiotics, and particularly to the nephrotoxic effects of these agents. The pimaricin was formulated in DMA/Intralipid™ to a stock drug concentration of 10 mg/ml, and then diluted with Intralipid™, so the doses (1.0 mg/kg/day in two dogs and 5.0 mg/kg/day in two other dogs) could be administered IV in a volume of 10 ml over 1 hour by pump through a cephalic vein catheter. To assure reproducibility of the experimental conditions, the infusions were staggered; one dog at each dose level was started on two consecutive days. The investigation was performed in male beagle dogs weighing 10–14 kg. The animals were not anesthetized but were restrained in a hanging sling during the drug infusion, which was performed at the same time daily for 14 consecutive days. EKGs were recorded and blood samples were obtained for determination of pimaricin concentrations prior to the drug infusion and at various times during and following the infusion on the first day and on the last day of drug infusion. Blood for analysis of liver and kidney function, as well as for differential and complete blood counts, and platelet counts, was obtained in the morning before the first drug infusion, and also on days 8 and 15.

All animals were allowed free access to food and water, but with some restriction to space and mobility, since we were concerned that parenterally administered pimaricin could be cardiotoxic and cause fatal arrhythmias in a fashion similar to that of AMB, another polyene antibiotic.

The drug was administered through the cephalic vein with good tolerance. The cannula and tubing were carefully flushed with heparinized saline after each injection to prevent clot formation and to prevent drug from adhering to the catheter wall and thus interfering with the blood sampling for routine chemistries and for the pharmacokinetic analysis.

Blood samples of 3 ml were drawn in heparinized tubes before drug infusion, and at 10, 30, 55, 65, 70, 80, and 100 min, and at 2, 4, 6, 12, 18, and 24 hours after the start of the infusion. The blood was centrifuged at 1,000×g for 10 min. and the plasma was separated and stored at −80° C. until assayed by HPLC.

Results and Discussion of the Data.

Pimaricin in Plasma and iv Drug Pharmacology.

Figure 10A:
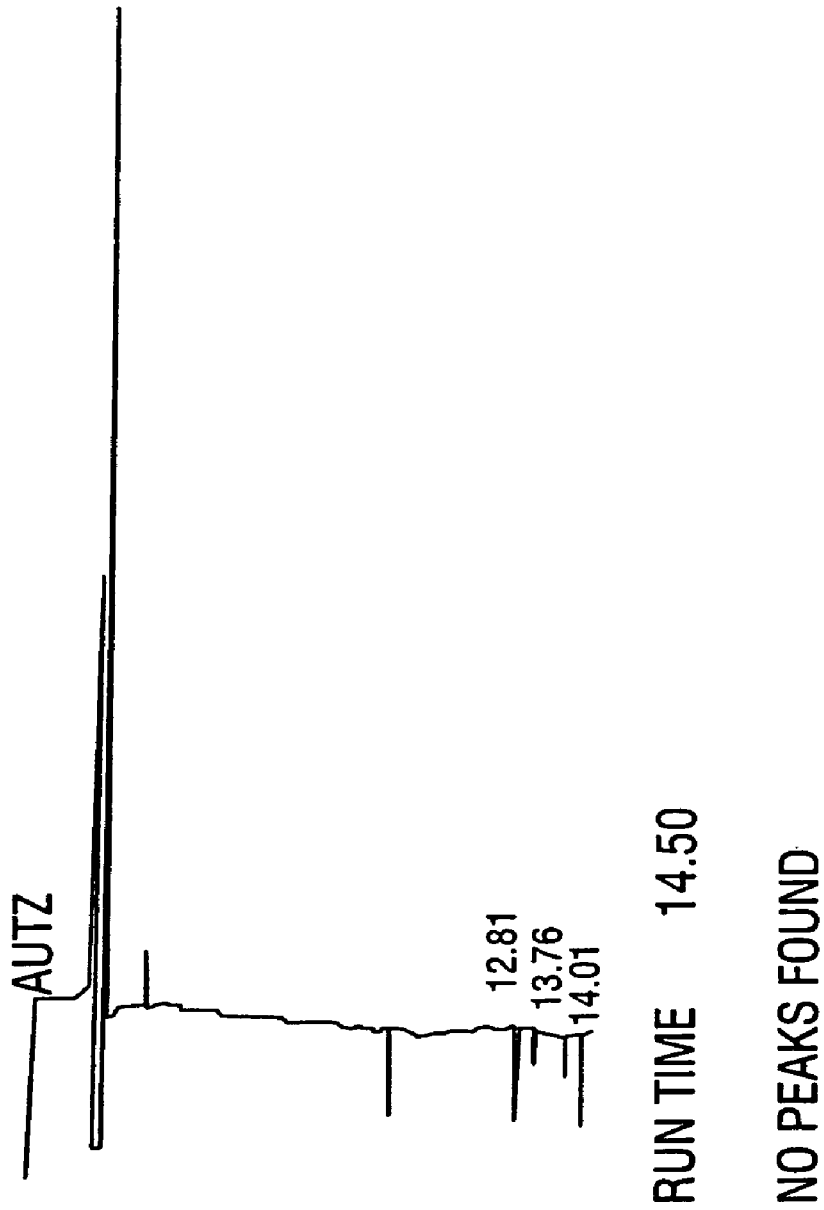
FIG. 10a: Plasma blank samples before the start of infusion.
Figure 10B:
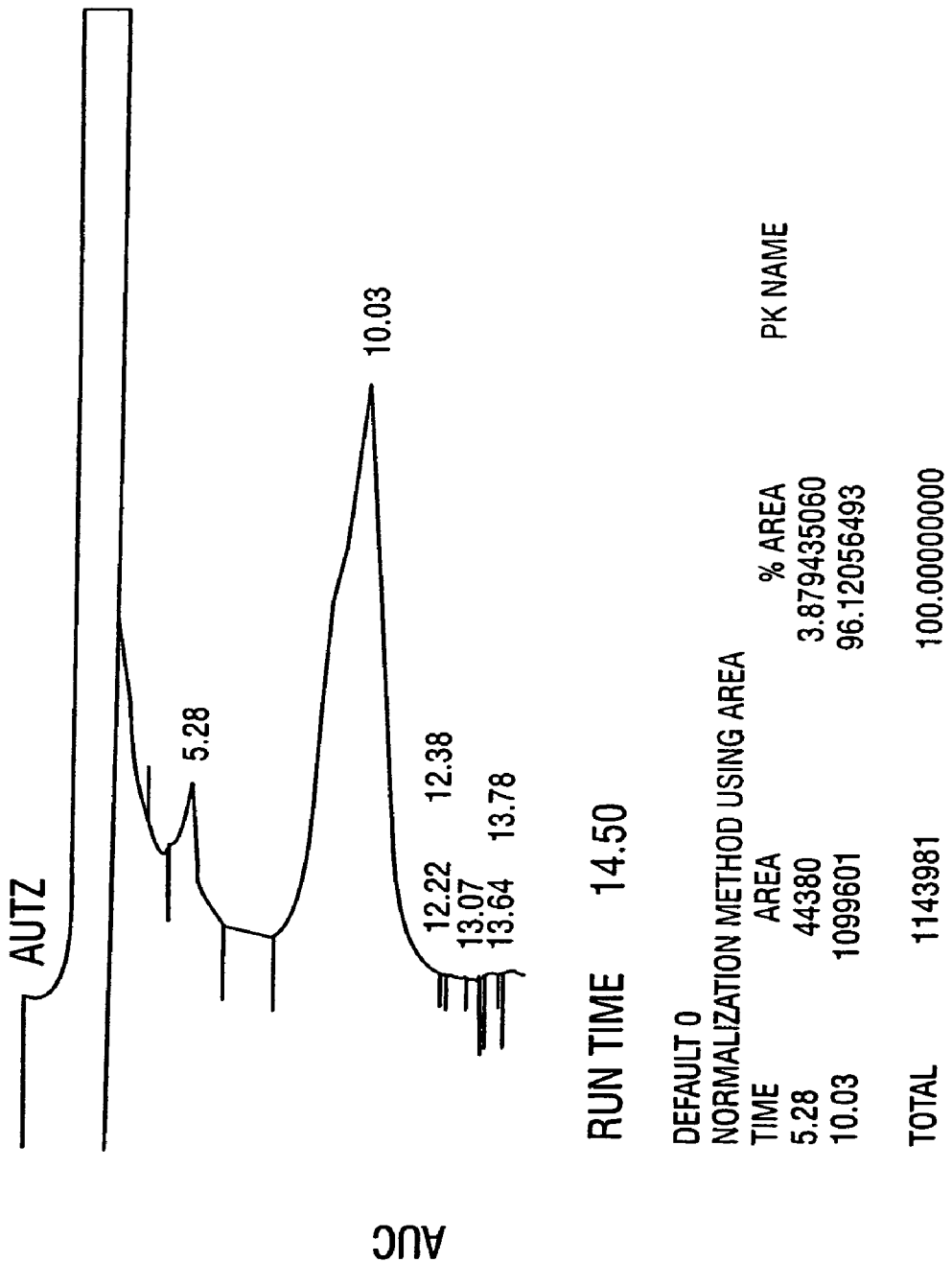
FIG. 10b: Sample from a dog injected with 5 mg/kg body weight of pimaricin. The drug was given over 1 hour iv and this blood sample was obtained 5 hours after drug infusion was completed. The sample was extracted and analyzed as described in the text.

The drug extraction with hexane and MeOH from plasma was essential to avoid interference from endogenous plasma components and to recover the maximum amount of drug. Chromatograms from blank plasma, pimaricin-spiked plasma, and one example of that obtained after extraction of a plasma sample from the current pharmacokinetic study are shown in FIG. 10. The pimaricin retention time in this system was 9.8–10.8 min. The recovery of pimaricin with the above described technique was 91±5% when human plasma was spiked in vitro with 10 μg/ml of drug. The assay was linear after drug extraction from plasma samples in the range from 50 ng/ml to 1.0 mg/ml. The drug recovery from canine plasma was 85±4%, with an accuracy of 98% and a limiting sensitivity of about 10 ng/ml. A standard curve was prepared in the concentration range from 100 ng/ml to 25 μg/ml (FIG. 11), and a good correlation was obtained between the plasma pimaricin concentration and peak AUC value ("AUC" refers to the area under the curve measurement that one gets as the exact reading from the fluorescence detector. I can be translated to drug concentration using a standard curve:

$$AUC=1.2209e+4+3.2994e+5x, r^2=1.00. \qquad \text{(Eq. 1)}$$

where e is the exponential function, x is the drug concentration that is sought, and $r^2$ is the correlation coefficient for the linear regression analysis for the ideal curve obtained from the actual data points in the observation interval.

Figure 12:
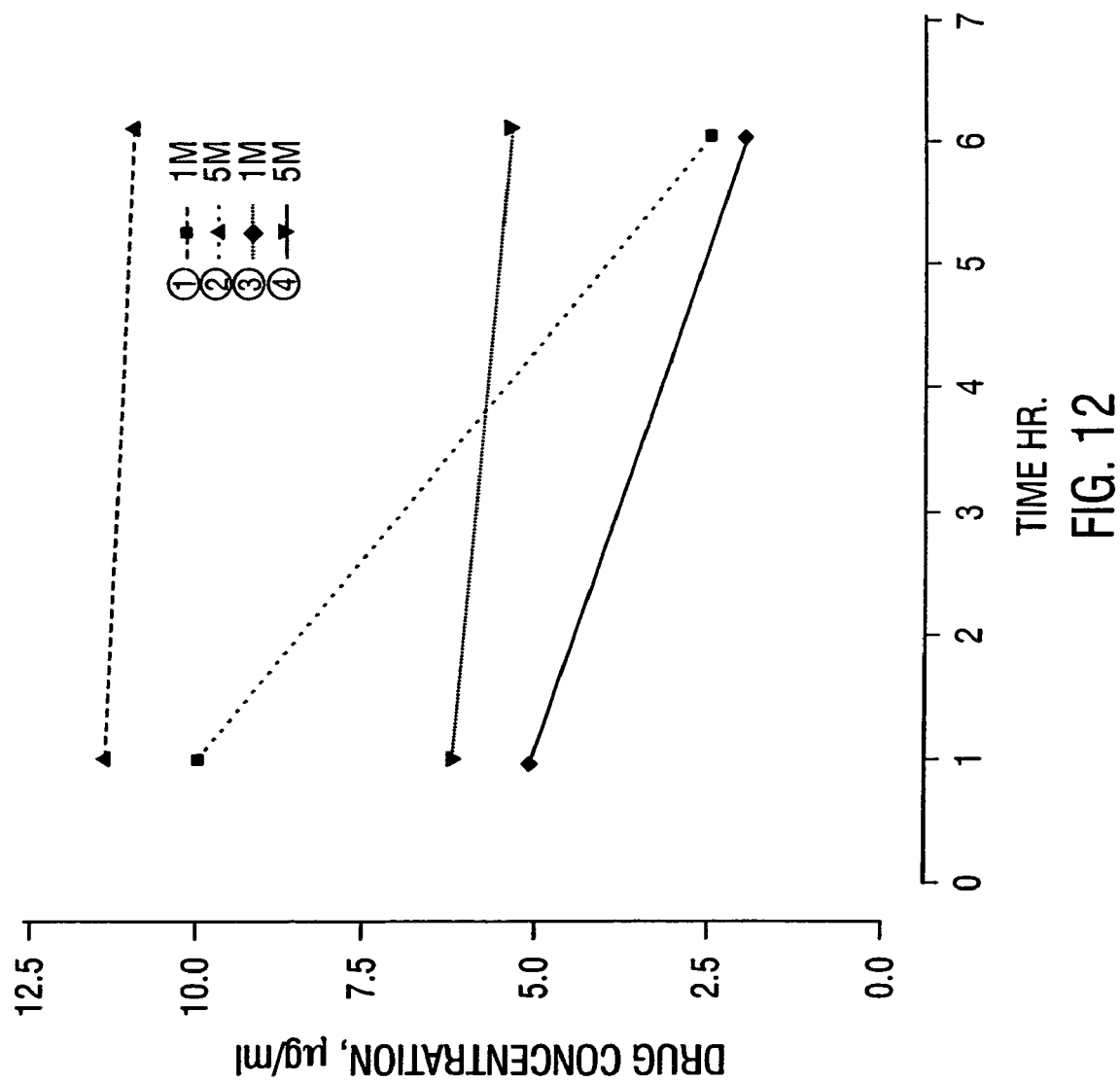
FIG. 12: Comparative plasma concentrations during and after infusion of pimaricin at 1 mg/kg, and 5 mg/kg in four beagle dogs. The samples were drawn just before the end of the 60 min infusion and 5 hours after the end of infusion. The different numbers and symbols, respectively, refer to the individual animals, and the 1 and 5 respectively refer to the dose of pimaricin administered per kg body weight.

The in vivo peak plasma pimaricin concentrations after iv administration of the above formulation was plotted for the two dose levels at the end of the 1 hour infusion and 5 hours later (FIG. 12); the measured concentrations are all within the in vitro range of sensitivity for the majority of the examined fungal isolates (see Tables 2 and 3).

Animal Experiment.

There were no clinically discernible cardiac arrhythmias assessed through clinical monitoring and serial EKGs before, during, and following the pimaricin infusions, and neither was there any detected impairment of hepatic or renal function over the 14-day experiment (Table 5). Group A consisted of two dogs (1 and 2) which were dosed at 1.0 and 5.0 mg/kg/day, respectively. Group B consisted of two dogs (3 and 4) which were also dosed at 1.0 and 5.0 mg/kg/day, respectively. Doses were administered to Group A on days 1–14 and to Group B on days 2–15. Samples were taken from Group A on day 0 (the day before treatment started), day 8 (after the first seven daily injections but before the eighth), and day 15 (the day after the final treatment). Samples were taken from Group B on day 1 (the day before treatment started), day 9 (after the first seven daily injections but before the eighth), and day 16 (the day after the final treatment).

TABLE 5

Serum chemistry values in beagles after daily intravenous infusions of Pimaricin over a 14-day period

| Group | Dog | Dose | Na | K | Cl | BUN | Creat | P | TP | Albu | DB | LDH | AST | ALT | TB | AP | GGT | Mg |
|---|---|---|---|---|---|---|---|---|---|---|---|---|---|---|---|---|---|---|
| Table 5A — Day 0 or Day 1 (baseline) | | | | | | | | | | | | | | | | | | |
| A | 1 | 1.0 | 139 | 4.5 | 105 | 13 | 0.8 | 3.9 | 5.9 | 3.4 | 0.0 | 518 | 84 | 52 | 0.3 | 195 | 1 | 1.3 |
| A | 2 | 5.0 | 142 | 4.6 | 107 | 14 | 1.4 | 3.0 | 6.0 | 3.5 | 0.0 | 247 | 36 | 31 | 0.2 | 84 | 2 | 1.2 |
| B | 3 | 1.0 | 148 | 5.7 | 112 | 21 | 1.2 | 4.8 | 6.5 | 3.9 | 0.0 | 467 | 40 | 38 | 0.2 | 88 | 1 | 1.8 |
| B | 4 | 5.0 | 146 | 4.7 | 109 | 15 | 1.1 | 3.6 | 6.6 | 3.7 | 0.0 | 196 | 33 | 68 | 0.3 | 261 | 2 | 1.7 |
| Table 5B — Day 8 or Day 9 | | | | | | | | | | | | | | | | | | |
| A | 1 | 1.0 | 143 | 4.9 | 110 | 18 | 0.7 | 3.8 | 5.6 | 3.0 | 0.0 | 597 | 63 | 32 | 0.1 | 174 | 5 | 1.9 |
| A | 2 | 5.0 | 122 | 5.9 | 75 | 90 | 1.8 | 6.4 | 8.2 | 3.9 | 0.2 | 624 | 122 | 98 | 0.5 | 1093 | 12 | 3.4 |
| B | 3 | 1.0 | 135 | 4.9 | 103 | 20 | 0.9 | 3.7 | 5.6 | 3.3 | 0.0 | 675 | 54 | 37 | 0.2 | 80 | 3 | 1.9 |
| B | 4 | 5.0 | 132 | 3.8 | 98 | 24 | 0.9 | 3.0 | 5.5 | 2.7 | 0.1 | 527 | 59 | 232 | 0.2 | 911 | 15 | 1.7 |
| Table 5C — Study termination (day 15 or day 16) | | | | | | | | | | | | | | | | | | |
| A | 1 | 1.0 | 143 | 5.1 | 113 | 20 | 0.8 | 3.6 | 5.4 | 3.1 | 0.0 | 345 | 54 | 33 | 0.2 | 109 | 3 | 1.8 |
| A | 2 | 5.0 | 111 | 10.3 | 71 | 247 | 3.5 | 17.5 | 8.6 | 4.2 | — | 751 | 545 | 205 | 1.0 | 625 | — | — |
| B | 3 | 1.0 | 144 | 5.2 | 111 | 20 | 1.1 | 4.6 | 5.5 | 3.5 | 0.0 | 211 | 33 | 34 | 0.1 | 56 | 3 | 2.0 |
| B | 4 | 5.0 | 144 | 4.0 | 108 | 21 | 0.9 | 3.2 | 5.3 | 2.9 | 0.0 | 63 | 26 | 64 | 0.2 | 424 | 8 | 1.6 |

Animal 2 died on day 12 of the study. Blood was obtained and analyzed, with the exception of levels listed as (--), immediately post-mortem. Abbreviations used in the table have the following meanings. Magnesium level indicated for animal 4 on day 9 is the average of two readings.

| | |
|---|---|
| Na | sodium |
| K | potassium |
| Cl | chloride |
| BUN | blood urea nitrogen |
| Creat | creatinine |
| P | phosphorus |
| TP | total protein |
| Albu | albumin |
| DB | direct bilirubin |
| LDH | lactic dehydrogenase |
| AST | serum aspartate aminotransferase |
| ALT | serum alanine aminotransferase |
| TB | total bilirubin |
| AP | alkaline phosphatase |
| GGT | gamma glutamyl transpeptidase |
| Mg | Magnesium |

TABLE 6

Hematologic values in beagles after daily intravenous infusions of Pimaricin over a 14-day period

| Group | Dog | Dose | PT | PTT | Fibr | FDP | RET | WBC | HGB | HCT | MCV | PLT | Neu | Lym | Mon | Eos | Baso |
|---|---|---|---|---|---|---|---|---|---|---|---|---|---|---|---|---|---|
| Table 6A — Day 0 or Day 1 (baseline) | | | | | | | | | | | | | | | | | |
| A | 1 | 1.0 | 6.0 | 13.5 | 420 | neg | 0.4% | 39.1 | 12.8 | 37.3 | 68.0 | 246 | 92.2 | 3.1 | 4.1 | 0.2 | 0.0 |
| A | 2 | 5.0 | 5.5 | 13.3 | 190 | neg | 0.1% | 12.1 | 14.4 | 41.5 | 67.3 | 388 | 65.4 | 26.4 | 3.8 | 3.6 | 0.3 |
| B | 3 | 1.0 | 6.6 | 15.8 | 330 | neg | 0.7% | 12.9 | 16.4 | 49.1 | 69.9 | 544 | 73.5 | 18.8 | 4.9 | 2.4 | 0.2 |
| B | 4 | 5.0 | 5.5 | 15.3 | 420 | neg | 0.4% | 5.8 | 17.2 | 50.6 | 70.3 | 208 | 52.7 | 28.8 | 14.1 | 4.1 | 0.1 |
| Table 6B — Day 8 or Day 9 | | | | | | | | | | | | | | | | | |
| A | 1 | 1.0 | 6.0 | 12.3 | 390 | neg | 4.6% | 21.9 | 11.6 | 35.0 | 71.0 | 346 | 80.0 | 10.4 | 7.1 | 1.8 | 0.2 |
| A | 2 | 5.0 | 7.0 | 15.3 | 555 | neg | 2.8% | 48.8 | 18.6 | 53.0 | 64.1 | 112 | 89.0 | 5.4 | 4.2 | 0.7 | 0.1 |
| B | 3 | 1.0 | 5.3 | 12.8 | 230 | neg | 6.9% | 15.2 | 12.6 | 37.9 | 70.3 | 358 | 65.2 | 23.6 | 6.9 | 3.7 | 0.2 |
| B | 4 | 5.0 | 5.8 | 13.5 | 430 | neg | 7.2% | 16.2 | 13.6 | 40.5 | 71.6 | 138 | 75.4 | 11.9 | 10.3 | 1.8 | 0.1 |
| Table 6C — Study termination (Day 15 or 16) | | | | | | | | | | | | | | | | | |
| A | 1 | 1.0 | 7.8 | 12.0 | 220 | neg | 2.1% | 14.2 | 11.0 | 33.4 | 72.4 | 255 | 80.0 | 14.0 | 3.9 | 1.8 | 0.1 |
| A | 2 | 5.0 | 10.8 | 23.5 | 330 | neg | 0.4% | 81.6 | 19.6 | 53.2 | 62.0 | 202 | 96.0 | 2.0 | 1.0 | 0 | 0 |
| B | 3 | 1.0 | 8.3 | 13.3 | 280 | neg | 0.9% | 14.5 | 12.3 | 37.0 | 71.3 | 421 | 65.4 | 25.2 | 4.4 | 4.6 | 0.1 |
| B | 4 | 5.0 | 8.3 | 13.0 | 310 | neg | 1.1% | 19.4 | 11.6 | 35.1 | 72.4 | 152 | 76.6 | 11.7 | 8.4 | 3.0 | 0.1 |

As mentioned above, animal 2 died on day 12 of the study. Blood was obtained and analyzed, with the exception of MCV which was calculated, immediately post-mortem. Abbreviations used in Table 6 have the following meanings.

| | |
|---|---|
| PT | prothrombin time |
| PTT | partial thromboplastin time |
| Fibr | fibrinogen |
| FDP | fibrin degradation products |
| RET | reticulocytes |
| WBC | white blood cell count |
| HGB | hemoglobin |
| HCT | hematocrit |
| MCV | mean corpuscular volume |
| PLT | platelet count |
| Neu | neutrophils |
| Lym | lymphocytes |
| Mon | monocytes |
| Eos | Eosinophils |
| Baso | Basophils |

We found mild signs of hemolysis in the form of a gradual lowering of hemoglobin and hematocrit levels and a slight increase in reticulocyte counts during the study (Table 6). There was, however, no sign of bone marrow suppression/toxicity assessed by the white blood cell count, platelet count, or fibrinogen levels or any of the coagulation parameters (see Table 6). (Normal values for various hematological and serum chemistry parameters are provided in reference 44.)

Our data demonstrate the successful design of pharmaceutically acceptable formulations of pimaricin, ones that are physiologically compatible with parenteral administration, with good tolerance and negligible toxicity, as demonstrated in the canine model. The intravenous infusion of one of the preparations in beagles provided plasma concentrations that reached and over many hours maintained fungicidal pimaricin concentrations without any discernible untoward effects on the animals' clinical performance or as detected by assessment of their hepatic or renal function during the 2-week experiment. It should be noted, that for this experiment we selected the "fresh" DMA/aqueous lipid formulation that had the highest concentration of an organic solvent, DMA, to allow for the least favorable scenario when considering the potential for adverse influence of the solvent system on hepatic and renal function, as well as on the hematopoietic and cardiovascular systems.

Our data obtained with several diverse formulations demonstrate conclusively that it should be feasible to introduce parenteral pimaricin in clinical therapy of systemic fungal infections including fusariosis, with the predictable attainment of antibiotic activity, and with a reasonable expectation of low normal organ toxicity. The inclusion of a lyophilization step in the formulation procedure significantly increased the stability/shelf-life of the final formulations. This step virtually eliminates the final use-preparation's content of the organic solvent, and we expect it not only to further reduce the risk of solvent system toxicity, but also to minimize the risk that the organic solvent could potentiate clinical adverse effects related to pimaricin.

It is apparent from the results that a dramatically improved bioavailability of pimaricin was provided. Further, this novel preparation yielded plasma drug concentrations and areas under the plasma concentration vs. time curses that were clearly fungicidal, based on comparisons with our in vitro sensitivity studies with pimaricin against several strains of *Aspergillus* spp., and *Candida* spp., but most importantly against *Fusarium* spp., since this fungus is typically multidrug resistant. The present invention makes it feasible to obtain beneficial effects of pimaricin against systemic mycoses with the potential for a major improvement in the outcome of such infections.

Compositions of the present invention can further include additional pharmaceutically acceptable carriers adjuvants, and/or biologically active substances. Compositions of the present invention, as described above, can be used in methods for treatment or prophylaxis of systemic fungal infections in mammals, particularly in humans. The methods involve administering to a mammal an amount of the compositions effective to prevent, eliminate, or control the fungal infection. The administering step can suitably be parenteral (preferably by intravenous injection). The compositions can also be administered intranasally as an aerosol. Such administration is preferably repeated on a timed schedule, and may be used in conjunction with other forms of therapy or prophylaxis, including methods involving administration of different biologically active agents to the subject. The dose administered of a composition in accordance with the present invention is preferably between approximately 0.1 and 100 mg/kg of body weight of the mammalian subject to which it is administered, most preferably between about 1–5 mg/kg.

The preceding description of specific embodiments of the present invention is not intended to be a complete list of every possible embodiment of the invention. Persons skilled in this field will recognize that modifications can be made to the specific embodiments described here that would be within the scope of the present invention.

REFERENCES

The following references, to the extent that they provide exemplary procedural or other details supplementary to those set forth herein, are specifically incorporated herein by reference.

1. Anaissie E J, Bodey G P, Rinaldi M G: Emerging fungal pathogens. Eur. J. Clin. Microbiol. Infect. Dis. 8:323–330, 1989.
2. Anaissie E J: Opportunistic mycoses in the immunocompromised host: experience at a cancer center and review. Clin. Infect. Dis. 14:S43–53, 1992.
3. Morrison V A, Haake R J, Weisdorf D J: The spectrum of non-*Candida* fungal infections following bone marrow transplantation. Medicine 72:78–89, 1993.
4. Morrison V A, Haake R J, Weisdorf D J: Non-*Candida* fungal infections after bone marrow transplantation: risk factors and outcome. Am. J. Med. 96:497–503, 1994.
5. Pfaller M, Wenzel R: Impact of the changing epidemiology of fungal infections in the 1990s. Europ. J. Clin. Microbiol. Infect. Dis. 11:287–291, 1992.
6. Blazar B R, Hurd D D, Snover D C, Alexander J W, McGlave P B: Invasive *Fusarium* infections in bone marrow transplant recipients. Am. J. Med. 77:645–651, 1984.
7. Uzun O, Anaissie E J: Antifungal prophylaxis in patients with hematologic malignancies: A reappraisal. Blood 86:2063–72, 1995.
8. Sande M A, Mandell G L: Antimicrobial agents, antifungal and antiviral agents, I. Antifungal agents: Amphotericin B. In: The pharmacological basis of therapeutics. Goodman Gilman A., Gilman L. S., Rall T. W., Murad F. (Eds.) $7^{th}$ Edition. MacMillan Publishing Company Inc. New York N.Y. pp 1219–1223, 1985.
9. Lopez-Berestein G., Mehta R, Hopfer R L, Mills K, Kasi L. Mehta K, Fainstein V, Luna M, Hersh E M. Juliano R: Treatment and prophylaxis of disseminated *Candida* albicans infections in mice with liposome-encapsulated amphotericin B. J. Infect Dis. 147:939–45. 1983.

10. Lopez-Berestein G., Hopfer R, Mehta R, Mehta K, Hersh E M, Juliano R L: Liposome-encapsulated amphotericin B for treatment of disseminated candidiasis in neutropenic mice. J. Infect Dis. 150:278–83. 1984.
11. Lopez-Berestein G. Bodey G P, Fainstein V, Keating M, Frankel L S, Zeluff B, Gentry L, Mehta K: Treatment of systemic fungal infections with liposomal amphotericin B. Arch. Int. Med. 149:2533–36. 1989.
12. Tollemar J, Ringden O, Andersson S, Sundberg B, Ljungman P, Sparreelid E, Tydén G: Prophylactic use of liposomal amphotericin B (AmBisome) against fungal infections: A randomized trial in bone marrow transplant recipients. Transplant Proc. 25:1495–97, 1993.
13. Boogaerts M A, Verhoef G E, Zachee P, Demuynck H, Verbist L, DeBeule K: Antifungal prophylaxis with itraconazole in prolonged neutropenia: Correlation with plasma levels. Mycoses 32:103, 1989 (Suppl. 1).
14. Vreugdenhil G, Van Dijke B J, Donnelly P, Novakova I R, Raemakers J M, Hoogkamp-Korstaje M A, Koster M, de Pauw B E: Efficacy of itraconazole in the prevention of fungal infections among neutropenic patients with hematologic malignancies and intensive chemotherapy. A double blind, placebo controlled study. Leukemia Lymphoma 11:353–358, 1994.
15. Struyk A R, Hoette I, Drost G, Waisvisz J M, van Eek T, Hoogenheide J C: Pimaricin, a new antifungal antibiotic. Antibiot. Ann. 878–85, 1957–1958.
16. Korteweg G C, Szabo K L, Rutten A M, Hoogerheide J C: Some pharmacological properties of pimaricin and possible clinical application of this antifungal antibiotic. Antibiot. Chemother. (Basel) 11:261–72, 1963.
17. Raab W P: Natamycin (pimaricin): Its properties and possibilities in medicine. Georg Thieme Publishers, Stuttgart, Germany. 1972.
18. Lavingia B, Dave S: Comparative study of amphotericin B, pimaricin and gentian violet on ocular fungi. Indian J. Ophthalmol. 34:73–77, 1986.
19. Natamycin, CAS Reg-No. 7681–93–8. Jun. 22, 1982. Code of Federal Regulations. Food and Drugs, §172.155, volume 21, revised Apr. 1, 1995.
20. Spiegel A. J. Noseworthy M. N.: Use of nonaqueous solvents in parenteral products. J. Pharm. Sci. 52:917–927, 1963.
21. Yalkowsky S. H., Roseman T. J.: Solubilization of drugs by cosolvents. In: Yalkowsky S. H. (Ed.): Techniques of solubilization of drugs. Pp. 91–134. Marcel Dekker Inc., New York, N.Y. 1981.
22. U.S. Department of Health and Human Services: NCI Investigational drugs. NIH Publication No. 84–2141, 1984.
23. Weiss A. J., Jackson L. G., Carabasi R. A., Mancall E. L., White J. C.: A phase I study of dimethylacetamide. Cancer Chemother. Rep., 16: 477–85, 1962.
24. Kim S. N.: Preclinical toxicology and pharmacology of dimethylacetamide with clinical notes. Drug Metab. Rev: 19:345–368 1988.
25. Lockard J. S., Levy R. H., Congdon W. C., DuCharme L. L.: Efficacy and toxicity of the solvent polyethylene glycol 400 in monkey model. Epilepsia 20:77–84, 1979.
26. Keating M. J., Holmes R., Lerner S., Ho D. H.: L-Asparaginase and PEG asparaginase—past, present and future. Leukemia and Lymphoma. 10:153–57, 1993.
27. McGann L: Differing actions of penetrating and non-penetrating cryoprotective agents. Cryobiology, 15:382–90, 1978.
28. Gorin N C: Collection, manipulation, and freezing of hemopoietic stem cells. Clin Haematol. 15:19–48, 1986.
29. Davis J M, Rowley S D: Autologous bone marrow graft processing. In: Sacher R A, McCarthy L J, Smit Siblinga Cth.: Processing of bone marrow for transplantation. American Association of Blood Banks, Arlington Va., 1990, pp. 41–62.
30. Gorin N C: Cryopreservation and storage of stem cells. In: Areman E M, Deeg J H, Sacher R A. Bone marrow and stem cell processing: A manual of current techniques. F. A Davis Company, Philadelphia Pa., 1992, pp. 292–362.
31. Fortner C L, Grove W R, Bowie D, Walker M D: Fat emulsion vehicle for intravenous administration of an aqueous insoluble drug. Am. J. Hosp. Pharm. 32:582–84, 1975.
32. Benet L. Z., and Sheiner L. B.: Pharmacokinetics: The dynamics of drug absorption, distribution, and elimination. In:The pharmacological basis of therapeutics. Goodman Gilman A.. Gilman L. S., Rall T. W., Murad F. (Eds.) $7^{th}$ Edition. MacMillan Publishing Company Inc. New York, N.Y. pp. 3–34, 1985.
33. Unpublished, Courtesy, of Gist-Brocades, Industrial Products Division, Delft. Holland.
34. Mann H. B., Whitney D. R.: On a test whether one of two random variables is stochastically larger than the other. Ann. Math. Statist. 18: 50–60, 1947.
35. Parthasarathy R, Sacks P G, Harris D, Brock H, Mehta K: Interaction of liposome-associated all-trans-retinoic acid with squamous carcinoma cells. Cancer Chemother. Pharmacol. 34:527–34, 1994.
36. Gallagher R, Collins S. Trujillo J, McCredie K B, Ahearn M, Tsai S, Anlakh G S. Ting R, Ruscetti F Gallo R: Characterization of the continuously differentiating myeloid cell line (HL-60) from a patient with acute promyelocytic leukemia. Blood 54:254–68, 1979.
37. Andersson B S, Beran M, Pathak S, Goodacre A, Barlogie B, McCredie K B: Ph-positive chronic leukemia with near-haploid conversion in vivo and establishment of a continuously growing cell line with similar cytogenetic pattern. Cancer Genetics and Cytogenet 24:335–43, 1987.
38. Andersson B S, Collins V P, Kurzrock R, Larkin D. W., Childs C, Ost A, Cork A, Trujillo J M, Beran M, Freirech E J, Siciliano M and Deisseroth A B: KBM-7; human myeloid leukemia cell line with double Philadelphia chromosomes but lacking normal BCR and c-ABL transcripts. Leukemia 9:2100–2108, 1995.
39. Hansen M. B., Nielsen S. E., Berg K.: Re-examination and further development of a precise and rapid dye method for measuring cell growth/cell kill. J. Immunol. Methods. 119:203–210, 1989.
40. Andersson B S, Sadeghi T, Siciliano M, Legerski R, Murray D: Nucleotide excision repair genes as determinants of cellular sensitivity to cyclophosphamide analogs. Cancer Chemother and Pharmacol, 38:406–416 (1996).
41. Hopfer R L, Mehta R, Lopez-Berestein G: Synergistic antifungal activity and reduced toxicity of liposomal amphotericin B combined with gramicidin S or NF. Antimicrobial Agents and Chemotherapy 31:1978–81, 1987.
42. Anaissie E., Paetznick V., Bodey G. P., Fluconazole susceptibility testing of *Candida* albicans: Microtiter method that is independent of inoculum size, temperature, and time of reading. Antimicrob Methods Chemother. 35:1641–46, 1991.
43. Napoli J L, Pramanik B C, Williams J B, Dawson M I, Hobbs P D: Quantification of retinoic acid by gas-liquid chromatography-mass spectrometry: total versus all-trans-retinoic acid in human plasma. J Lipid Res. 26:387–92, 1985.

44. Duncan J R, Prasse K W: Veterinary Medicine Clinical Pathology. 2d ed. Iowa State University Press, Ames, Iowa. 1988.

What is claimed is:

1. A method of treating a fungal infection in a mammal, comprising:
   a) obtaining an amount of pimaricin or a salt thereof that is effective to inhibit the growth of a fungal infection in a mammal;
   b) mixing said pimaricin in a pharmaceutically acceptable dipolar aprotic solvent and/or acid to prepare a composition;
   c) mixing the composition of step b) in a pharmaceutically acceptable aqueous secondary solvent;
   d) removing more than 95% by weight of the dipolar aprotic solvent and/or acid from the composition; and
   e) administering to the mammal the composition of step d) in an amount effective to treat the fungal infection.

2. The method of claim 1, where the administration is intravascular or intravenous.

3. The method of claim 1, where the aprotic solvent is N,N-dimethylacetamide.

4. The method of claim 1, where the aqueous secondary solvent is an aqueous lipid emulsion.

5. The method of claim 4, where the aqueous lipid emulsion comprises a lipid component that includes at least one vegetable oil and at least one fatty acid.

6. The method of claim 5, where the lipid component comprises at least about 5% by weight soybean oil and at least about 50% by weight fatty acids.

7. The method of claim 1, where the secondary solvent is selected from the group consisting of water, saline solution, and dextrose solution.

8. A method of treating a fungal infection in a mammal, comprising:
   a) obtaining an amount of pimaricin or a salt thereof effective to inhibit the growth of a fungal infection in a mammal;
   b) mixing said pimaricin in N,N-dimethylacetamide to prepare a composition;
   c) mixing the composition of step b) with an aqueous lipid emulsion that comprises at least one vegetable oil and at least one fatty acid;
   d) removing more than 95% by weight of the N,N-dimethylacetamide from the composition; and
   e) administering to the mammal the composition of step d) in an amount effective to treat the fungal infection.

9. The method of claim 8, wherein the process further comprises mixing the composition in a pharmaceutically acceptable aqueous solvent.

10. A method of treating a funga infection in a mammal comprising:
    a) obtaining an amount of pimaricin or a salt thereof that is effective to inhibit the growth of a systemic infection in a mammal;
    b) mixing said pimaricin in acetic acid;
    c) mixing the composition of step b) in a pharmaceutically acceptable aqueous secondary solvent;
    d) removing more than 95% by weight of the acetic acid from the composition; and
    e) administering to the mammal the composition of step d) in an amount effective to treat the fungal infection.

11. The method of claim 10, wherein the pharmaceutically acceptable aqueous secondary solvent is a aqueous lipid emulsion.

12. The method of claim 11, where the aqueous lipid emulsion comprises a lipid component that includes at least one vegetable oil and at least one fatty acid.

13. The method of claim 12, where the lipid component comprises at least about 5% by weight soybean oil and at least about 50% by weight fatty acids.

14. The method of claim 10, where the secondary solvent is water.

15. The method of claim 10, where the secondary solvent is saline solution.

16. The method of claim 10, where the secondary solvent is dextrose solution.

17. A method of treating a fungal infection in a mammal, comprising the step of administering to the mammal a composition that is prepared by the process comprising:
    a) obtaining an amount of pimaricin or a salt thereof that is effective to inhibit the growth of a fungal infection in a mammal;
    b) mixing said pimaricin in acetic acid;
    c) mixing the composition of step b) in an aqueous lipid emulsion;
    wherein the fungal infection in the mammal is treated.

18. The method of claim 17, wherein the process comprises removing more than 95% of said acetic acid from the composition.

19. The method of claim 18, wherein the process further comprises reconstitution in a pharmaceutically acceptable parenteral solution.

20. The method of claim 17, where the aqueous lipid emulsion comprises a lipid component that includes at least one vegetable oil and at least one fatty acid.

21. The method of claim 20, where the lipid component comprises at least about 5% by weight soybean oil and at least about 50% by weight fatty acids.

22. The method of claim 17, wherein the process further comprises mixing the composition in a pharmaceutically acceptable parenteral aqueous solvent.

\* \* \* \* \*

UNITED STATES PATENT AND TRADEMARK OFFICE
CERTIFICATE OF CORRECTION

PATENT NO. : 7,220,726 B2  Page 1 of 1
APPLICATION NO. : 10/439252
DATED : May 22, 2007
INVENTOR(S) : Andersson et al.

It is certified that error appears in the above-identified patent and that said Letters Patent is hereby corrected as shown below:

Claim 10, column 23, line 51, delete "funga" and insert --fungal-- therefor.

Signed and Sealed this

Twenty-eighth Day of August, 2007

JON W. DUDAS
*Director of the United States Patent and Trademark Office*